(12) United States Patent
Zamore et al.

(10) Patent No.: US 9,879,253 B2
(45) Date of Patent: *Jan. 30, 2018

(54) METHODS AND COMPOSITIONS FOR ENHANCING THE EFFICACY AND SPECIFICITY OF SINGLE AND DOUBLE BLUNT-ENDED SIRNA

(71) Applicant: UNIVERSITY OF MASSACHUSETTS, Boston, MA (US)

(72) Inventors: Phillip D. Zamore, Northboro, MA (US); Dianne Schwarz, Watertown, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/271,038

(22) Filed: May 6, 2014

(65) Prior Publication Data

US 2014/0287491 A1    Sep. 25, 2014

Related U.S. Application Data

(63) Continuation of application No. 13/270,920, filed on Oct. 11, 2011, now abandoned, which is a continuation of application No. 11/022,055, filed on Dec. 22, 2004, now abandoned.

(60) Provisional application No. 60/532,116, filed on Dec. 22, 2003.

(51) Int. Cl.
C12N 15/11      (2006.01)
C12N 15/113     (2010.01)

(52) U.S. Cl.
CPC .......... *C12N 15/113* (2013.01); *C12N 15/111* (2013.01); *C12Y 115/01001* (2013.01); *C12N 2310/14* (2013.01); *C12N 2320/50* (2013.01)

(58) Field of Classification Search
None
See application file for complete search history.

(56) References Cited

U.S. PATENT DOCUMENTS

| | | |
|---|---|---|
| 6,506,559 B1 | 1/2003 | Fire et al. |
| 7,459,547 B2 | 12/2008 | Zamore et al. |
| 7,595,387 B2 | 9/2009 | Leake et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,090,542 B2 | 1/2012 | Khvorova et al. |
| 8,304,530 B2 | 11/2012 | Zamore |
| 8,309,704 B2 | 11/2012 | Zamore |
| 8,309,705 B2 | 11/2012 | Zamore |
| 8,329,892 B2 | 12/2012 | Zamore |
| 2002/0086356 A1 | 7/2002 | Tuschl et al. |
| 2002/0173478 A1 | 11/2002 | Gewirtz |
| 2003/0108923 A1 | 6/2003 | Tuschl et al. |
| 2003/0143732 A1 | 7/2003 | Fosnaugh et al. |
| 2003/0180756 A1* | 9/2003 | Shi et al. ............ 435/6 |
| 2004/0002153 A1 | 1/2004 | Monia et al. |
| 2004/0053411 A1 | 3/2004 | Cullen et al. |
| 2004/0096843 A1 | 5/2004 | Rossi et al. |
| 2004/0137471 A1 | 7/2004 | Vickers et al. |
| 2004/0175703 A1 | 9/2004 | Kreutzer et al. |
| 2004/0180351 A1 | 9/2004 | Giese et al. |
| 2004/0192629 A1 | 9/2004 | Xu et al. |
| 2004/0203145 A1 | 10/2004 | Zamore et al. |
| 2004/0214198 A1 | 10/2004 | Rana |
| 2004/0224328 A1 | 11/2004 | Prydz et al. |
| 2004/0229266 A1 | 11/2004 | Tuschl et al. |
| 2004/0248299 A1 | 12/2004 | Jayasena et al. |
| 2004/0259247 A1 | 12/2004 | Tuschl et al. |
| 2004/0259248 A1 | 12/2004 | Tuschl et al. |
| 2005/0020521 A1 | 1/2005 | Rana |
| 2005/0026278 A1 | 2/2005 | Tuschl et al. |
| 2005/0037988 A1 | 2/2005 | Zamore et al. |
| 2005/0059005 A1 | 3/2005 | Tuschl et al. |
| 2005/0181382 A1 | 8/2005 | Zamore et al. |
| 2005/0182005 A1 | 8/2005 | Tuschl et al. |
| 2005/0186586 A1 | 8/2005 | Zamore et al. |
| 2005/0227256 A1 | 10/2005 | Hutvagner et al. |
| 2005/0227940 A1 | 10/2005 | Rossi et al. |
| 2005/0234007 A1 | 10/2005 | Tuschl et al. |
| 2005/0244858 A1 | 11/2005 | Rossi et al. |
| 2005/0246794 A1 | 11/2005 | Khvorova et al. |

(Continued)

FOREIGN PATENT DOCUMENTS

| | | |
|---|---|---|
| AU | 2004220556 A1 | 9/2004 |
| CA | 2432341 A1 | 7/2002 |

(Continued)

OTHER PUBLICATIONS

U.S. Appl. No. 14/294,817, filed Jun. 3, 2014, 2014/0322813, Oct. 30, 2014.
U.S. Appl. No. 13/654,199, filed Oct. 17, 2012, 2013/0309767, Nov. 21, 2013.
U.S. Appl. No. 13/270,920, filed Oct. 11, 2011, 2012/0322846, Dec. 20, 2012.
Paddison, Patrick J. et al., "Short hairpin RNAs (shRNAs) induce sequence-specific silencing in mammalian cells," Genes & Development, vol. 16:948-958 (2002).
Pal-Bhadra, Manika et al., "RNAi Related Mechanisms Affect both Transcriptional and Posttranscriptional Transgene Silencing in Drosophila," Molecular Cell. vol. 9:315-327, (2002).
Park, Wonkeun et al., "Carpel Factory, a Dicer Homolog, and HEN1, a Novel Protein, Act in microRna Metabolism in *Arabidopsis thaliana*," Current Biology, vol. 12:1484-1495, (2002).
Parker, James S. et al., "Structural insights into mRNA recognition from a PIWI domain-siRNA guide complex," Nature, vol. 434:663-666 (2005).

(Continued)

*Primary Examiner* — Dana H Shin
(74) *Attorney, Agent, or Firm* — Lathrop Gage LLP; James H. Velema, Esq.

(57) ABSTRACT

The present invention provides methods of enhancing the efficacy and specificity of RNAi using single or double blunt-ended siRNA. The invention also provides single and double-blunt ended siRNA compositions, vectors, and transgenes containing the same for mediating silencing of a target gene. Therapeutic methods are also featured.

10 Claims, 11 Drawing Sheets

(56) References Cited

U.S. PATENT DOCUMENTS

| | | |
|---|---|---|
| 2005/0256072 A1 | 11/2005 | Aronin et al. |
| 2005/0273868 A1 | 12/2005 | Rana |
| 2005/0277610 A1 | 12/2005 | Rossi et al. |
| 2006/0009402 A1 | 1/2006 | Zamore et al. |
| 2006/0069050 A1 | 3/2006 | Rana |
| 2006/0128650 A1 | 6/2006 | Xu |
| 2006/0134787 A1 | 6/2006 | Zamore et al. |
| 2006/0166910 A1 | 7/2006 | Tuschl et al. |
| 2006/0178334 A1 | 8/2006 | Rossi et al. |
| 2006/0212950 A1 | 9/2006 | Tuschl et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0104688 A1 | 5/2007 | Rossi et al. |
| 2007/0111228 A1 | 5/2007 | Jayasena et al. |
| 2007/0207974 A1 | 9/2007 | Khvorova et al. |
| 2007/0265220 A1 | 11/2007 | Rossi et al. |
| 2008/0318896 A1 | 12/2008 | Zamore et al. |
| 2009/0018321 A1 | 1/2009 | Rossi et al. |
| 2009/0029466 A1 | 1/2009 | Rossi et al. |
| 2009/0029936 A1 | 1/2009 | Rossi et al. |
| 2009/0035854 A1 | 2/2009 | Rossi et al. |
| 2009/0036661 A1 | 2/2009 | Rossi et al. |
| 2009/0043083 A1 | 2/2009 | Rossi et al. |
| 2009/0043085 A1 | 2/2009 | Rossi et al. |
| 2010/0184826 A1 | 7/2010 | Zamore et al. |
| 2010/0184827 A1 | 7/2010 | Zamore et al. |
| 2010/0184828 A1 | 7/2010 | Zamore et al. |

FOREIGN PATENT DOCUMENTS

| | | |
|---|---|---|
| CA | 2432350 A1 | 7/2002 |
| DE | 10160151 A1 | 6/2003 |
| EP | 1389637 A1 | 2/2004 |
| EP | 1527176 B1 | 5/2005 |
| EP | 1857547 A2 | 11/2007 |
| WO | 01/75164 A2 | 10/2001 |
| WO | 02/44321 A2 | 6/2002 |
| WO | 02/055692 A2 | 7/2002 |
| WO | 02/055693 A2 | 7/2002 |
| WO | 03/020931 A2 | 3/2003 |
| WO | 03/035869 A1 | 5/2003 |
| WO | 03/064621 A2 | 8/2003 |
| WO | 03/068797 A1 | 8/2003 |
| WO | 2003/093441 A2 | 11/2003 |
| WO | 04/015107 A2 | 2/2004 |
| WO | 04/027030 A2 | 4/2004 |
| WO | 04/029212 A2 | 4/2004 |
| WO | 04/045543 A2 | 6/2004 |
| WO | 04/046324 A2 | 6/2004 |
| WO | PCT/US04/17130 | 6/2004 |
| WO | PCT/US04/17256 | 6/2004 |
| WO | 04/061083 A2 | 7/2004 |
| WO | 04/063375 A1 | 7/2004 |
| WO | 04/064737 A2 | 8/2004 |
| WO | 04/080406 A2 | 9/2004 |
| WO | 05/001043 A2 | 1/2005 |
| WO | 05/062937 A2 | 7/2005 |
| WO | 05/069987 A2 | 8/2005 |
| WO | 05/079532 A2 | 9/2005 |
| WO | 05/079533 A2 | 9/2005 |
| WO | 05/089287 A2 | 9/2005 |
| WO | 06/015389 A2 | 2/2006 |
| WO | 08/136902 A1 | 11/2008 |

OTHER PUBLICATIONS

Parrish, Susan et al., "Functional Anatomy of a dsRNA Trigger: Differential Requirement for the Two Trigger Strands in RNA Interference," Molecular Cell, vol. 6:1077-1087 (2000).

Patzel, Volker et al, "Design of siRNAs producing unstructured guide-RNAs results in improved RNA interference efficiency," Nature Biotechnology, vol. 23(11):1440-1444 (2005).

Persengiev, Stephan P. et al., "Nonspecific, concentration-dependent stimulation and repression of mammalian gene expression by small interfering RNAs (siRNAs)," RNA, vol. 10:12-18 (2004).

Pham, John W. et al., "A Dicer-2-Dependent 80S Complex Cleaves Targeted mRNAs during RNAi in *Drosophila*," Cell, vol. 117:83-94 (2004).

Pillai, Ramesh S. et al., "Tethering of human Ago proteins to mRNA mimics the miRNA-mediated repression of protein synthesis," RNA, vol. 10:1518-1525 (2004).

Poy, Matthew N. et al., "A pancraetic islet-specific microRNA regulates insulin secretion," Nature, vol. 432:226-230 (2004).

Pusch, O. et al., "Nucleotide sequence homology requirements of HIV-1-specific short hairpin RNA," Nucleic Acids Res., vol. 31(22):6444-6449 (2003).

Rand, Tim A. et al., "Argonaute2 Cleaves the Anti-Guide Strand of siRNA during RISC Activation," Cell, vol. 123:621-629 (2005).

Rasmussen, M.H. et al., "Tumor model-specific proviral insertional mutagenesis of the Fos/Jdp2/Batf locus," Virology, vol. 337:353-364 (2005).

Reich, Samuel J. et al, "Small Interfering RNA (siRNA) targeting VEGF Effectively Inhibits Ocular Neovascularization in a Mouse Model," Molecular Vision, vol. 9, 210-216 (2003).

Reinhart, Brenda J. et al., "MicroRNAs in plants," Genes & Development, vol. 16:1616-1626 (2002).

Reinhart, Brenda J. et al., "The 21-nucleotide let-7 RNA regulates developmental timing in Caenorhabditis elegans," Nature, vol. 403:901-906 (2000).

Reynolds, A. et al., "Rational siRNA design for RNA interference," Nat. Biotechnol., vol. 22(3):326-330 (2004).

Rhoades, Matthew W. et al., "Prediction of Plant MicroRNA Targets," Cell, vol. 110:513-520 (2002).

Rivas, Fabiola V. et al., "Purified Argonaute2 and an siRNA form recombinant human RISC," Nature Structural & Molecular Biology, vol. 12(4):340-349 (2005).

Rose, Scott D. et al., "Functional polarity is introduced by Dicer processing of short substrate RNAs," Nucleic Acids Research, vol. 33(13):4140-4156 (2005).

Ruvkun, Gary, "Glimpses of a Tiny RNA World," Science, vol. 294:797-799, (2001).

Sahasrabudhe, Parag V. et al., "Solution Structures of 5-Fluorouracil-Substituted RNA Duplexes Containing G-U Wobble Base Pairs," Biochemistry, vol. 36:5981-5991 (1997).

Sasaki, Takashi et al., "Identification of eight members of the Argonaute family in the human genomes," Genomics, vol. 82:323-330 (2003).

Saxena, Sandeep et al., "Small RNAs with Imperfect Match to Endogenous mRNA Repress Translation," The Journal of Biological Chemistry, vol. 278(45):44312-44319 (2003).

Scadden, A.D.J. et al., "RANi is antagonized by A®l hyper-editing," EMBO reports, vol. 2(12):1109-1111 (2001).

Scherer, Lisa et al., "Therapeutic Applications of RNA Interference: Recent Advances in siRNA Design," Advances in Genetics, vol. 52:1-21 (2004).

Scherer, Lisa J. et al., "Approaches for the sequence-specific knockdown of mRNA," Nature Biotechnology, vol. 21 (12):1457-1465 (2003).

Scherer, Lisa J. et al., "Rapid Assessment of Anti-HIV siRNA Efficacy Using PCR-Derived Pol III shRNA Cassettes," Molecular Therapy, vol. 10(3):597-603 (2004).

Scherer, Lisa J. et al., "Recent Applications of RNAi in Mammalian Systems," Current Pharmaceutical Biotechnology, vol. 5:355-360 (2004).

Scherr, Michaela et al., "Specific inhibition of bcr-abl gene expression by small interfering RNA," Blood, vol. 101 (4):1566-1569 (2003).

Schmidt, Charlie et al., "Negotiating the RNAi patent thicket," Nature Biotechnology, vol. 25(3):273-275 (2007).

Schubert, Steffen et al., "Local RNA Target Structure Influences siRNA Efficacy: Systematic Analysis of Intentionally Designed Binding Regions," J. Mol. Biol., vol. 348:883-893 (2005).

(56) References Cited

OTHER PUBLICATIONS

Schwarz, D.S. et al., "Asymmetry in the assembly of the RNAi enzyme complex," Cell, vol. 115(2):199-208 (2003).
Schwarz, D.S. et al., "The RNA-induced silencing complex is a Mg2+-dependent endonuclease," Curr. Biol., vol. 14 (9):787-791 (2004).
Schwarz, D.S. et al., "Why do miRNAs live in the miRNP?" Genes Dev., vol. 16(9):1025-1031 (2002).
Schwarz, Dianne S. et al., "Designing siRNA That Distinguish between Genes That Differ by a Single Nucleotide," PLoS Genetics, vol. 2(9):1-12 (2006).
Schwarz, Dianne S. et al., "Evidence that siRNAs Function as Guides, Not Primers, in the Drosophila and Human RNAi Pathways," Molecular Cell, vol. 10:537-548 (2002).
Seggerson, Kathy et al., "Two Genetic Circuits Repress the Caenorhabditis elegans Heterochronic Gene lin-28 after Translation Initiation," Developmental Biology, vol. 243:215-225 (2002).
Semizarov, D. et al., "Specificity of short interfering RNA determined through gene expression signatures," PNAS, vol. 100(11):6347-6352 (2003).
Slack, Frank J. et al., "The lin-41 RBCC Gene Acts in the C. elegans Heterochronic Pathway between the let-7 Regulatory RNA and the LIN-29 Transcription Factor," Molecular Cell, vol. 5:659-669 (2000).
Sledz, Carol A. et al., "Activation of the interferon system by short-interfering RNAs," Nature Cell Biology, vol. 5 (9):834-838 (2003).
Smart, Nicola et al., "A rapid and sensitive assay for quantification of siRNA efficiency and specificity," Biol. Proced., vol. 7(1):1-7 (2005).
SnØve, Ola Jr. et al., "Chemical Modifications Rescue Off-Target Effects of RNAi," ACS Chemical Biology, vol. 1 (5):274-276 (2006).
Song, E. et al., "Intrahepatic Gene Silencing by RNA Interference," Gastroenterology, vol. 126(1):356-358 (2004).
Song, Erwei et al., "RNA interference targeting Fas protects mice from fulminant hepatitis," Nature Medicine, vol. 9 (3):347-351 (2003).
Song, Ji-Joon et al., "Crystal Structure of Argonaute and Its Implications for RISC Slicer Activity," Science, vol. 305:1434-1410 (2004).
Sontheimer, Erik J. et al., "Argonaute Journeys into the Heart of RISC," Science, vol. 305:1409-1410 (2004).
Soutschek, Jurgen et al, "Therapeutic Silencing of an Endogenous Gene by Systemic Administration of Modified si RNAs," Nature Publishing Group, vol. 432, 173-178 (2004).
Stark, Alexander et al., "Identification of Drosophila MicroRNA Targets," PLOS Biology, vol. 1(3):397-409 (2003).
Sundaralingam, Muttaiya et al., "Hydrogen and hydration of DNA and RNA oligonucleotides," Biophysical Chemistry, vol. 95:273-282 (2002).
Request for Ex Parte Reexamination Transmittal Form for U.S. Pat. No.7,772,203, pp. 1-206, dated Aug. 16, 2010.
Supplementary European Search Report for Application No. EP04753864, dated Mar. 5, 2007.
Written Opinion for Application No. PCT/US2005/029011, dated Apr. 13, 2006.
Lagos-Quintana, Mariana et al., "Identification of Novel Genes Coding for Small Expressed RNAs," Science, vol. 294:853-858 (2001).
Lagos-Quintana, Mariana et al., "Identification of Tissue-Specific MicroRNAs from Mouse," Current Biology, vol. 12:735-739 (2002).
Lagos-Quintana, Mariana et al., "New microRNAs from mouse and human," RNA, vol. 9:175-179 (2003).
Lai, E.C., "Micro RNAs are complementary to 3' UTR sequence motifs that mediate negative post-transcriptional regulation," Nat. Genet., vol. 30(4):363-364 (2002).

Lau, Nelson C. et al., "An Abundant Class of Tiny RNAs with Probable Regulatory Roles in Caenorhabditis elegans," Science, vol. 294:858-862 (2001).
Lee, Rosalind C. et al., "An Extensive Class of Small RNAs in Caenorhabditis elegans," Science, vol. 294:862-864 (2001).
Lee, Rosalind C. et al., "The C. elegans Heterochronic Gene lin-4 Encodes Small RNAs with Antisense Complementarity to lin-14," Cell, vol. 75:843-854 (1993).
Lewin, Benjamin, Genes VII, Oxford University Press, Oxford, p. 9 (2000).
Lewis, Benjamin P. et al., "Prediction of Mammalian MicroRNA Targets," Cell, vol. 115:787-798 (2003).
Lewis, David L. et al., "Efficient delivery of siRNA for inhibition of gene expression in postnatal mice," Nature Genetics, vol. 32:107-108 (2002).
Li, Bao-jian et al., "Using siRNA in Pophylactic and Therapeutic Regimens Against SARS Coronavirus in Rhesus Macaque," Nature Medicine, vol. 11(9):944-951 (2005).
Li, Wan Xiang et al., "Viral suppressors of RNA silencing," Current Opinion in Biotechnology. vol. 12:150-154, (2001).
Liang, Xue-hai et al., "Small nuclear RNA interference induced by antisense or double-stranded RNA in trypanosomatids," PNAS, vol. 100(13):7521-7526 (2003).
Lieberman, Judy et al., "Interfering with disease: opportunities and roadblocks to harnessing RNA interference," Trends in Molecular Medicine, vol. 9(9):397-403 (2003).
Lim, Lee P. et al, "Microarray analysis shows that some microRNAs downregulate large numbers of target mRNAs," Nature, vol. 433:769-773 (2005).
Lim, Lee P. et al., "The microRNAs of Caenorhabditis elegans," Genes & Development, vol. 17:991-1008 (2003).
Lim, Lee P. et al., "Vertebrate MicroRNA Genes," Science, vol. 299:1540 (2003).
Liu, Jidong et al., "Argonaute2 Is the Catalytic Engine of Mammalian RNAi," Science, vol. 305:1437-1441 (2004).
Liu, Qinghua et al., "R2D2, a Bridge Between the Initiation and Effector Steps of the Drosophila RNAi Pathway," Science, vol. 301:1921-1925 (2003).
Llave, Cesar et al., "Cleavage of Scarecrow-like mRNA Targets Directed by a Class of Arabidopsis miRNA," Science . vol. 297:2053-2056, (2002).
Lodish, Harvey et al., Molecular Cell Biology, Fourth Edition, Sara Tenney (Ed.), W.H. Freeman and Company, New York, p. 103 (2001).
Long, Dang et al., "Potent effect of target structure on microRNA function," Nature Structural & Molecular Biology, vol. 14(4):287-294 (2007).
Luo, Kathy Q. et al., "The gene-silencing efficiency of siRNA is strongly dependent on the local structure of mRNA at the targeted region," Biochemical and Biophysical Research Communications, vol. 318:303-310 (2004).
Mallory, Allison C. et al, "MicroRNA control of PHABULOSA in leaf development: importance of pairing to the microRNA 5' region," The EMBO Journal, vol. 23:3356-3364 (2004).
Martens, Henrik et al., "RNAi in Dictyostelium : The Role of RNA-directed RNA Polymerases and Double-stranded RNase," Molecular Biology of the Cell . vol. 13:445-453, (2002).
Martinez, J. et al., "Single-stranded antisense siRNAs guide target RNA cleavage in RNAi," Cell, vol. 110 (5):563-574 (2002).
Martinez, Javier et al., "RISC is a 5' phosphomonoester-producing RNA endonuclease," Genes & Development, vol. 18:975-980 (2004).
Martinez, Luis Alfonso et al, "Synthetic small inhibiting RNAs: Efficient tolls to inactivate oncogenic mutations and restore p53 pathways," PNAS, vol. 99(23):14849-14854 (2002).
Matranga, Christian et al., "Passenger-Strand Cleavage Facilitates Assembly of siRNA into Agog-Containing RNAi Enzyme Complexes," Cell, vol. 123:607-620 (2005).
McCaffrey, Anton P. et al., "RNA interference in adult mice," Nature, vol. 418:38-39 (2002).
McConnell, Jane R. et al., "Role of PHABULOSA and PHAVOLUTA in determining radial patterning in shoots," Nature . vol. 411:709-713, (2001).

(56) References Cited

OTHER PUBLICATIONS

McManus, M.T. et al., "Gene silencing using micro-RNA designed hairpins," RNA, vol. 8(6):842-850 (2002).
McManus, Michael T. et al., "Gene Silencing in Mammals by Small Interfering RNAs," Nature Reviews Genetics, vol. 3:737-747 (2002).
Meister, G. et al., "Sequence-specific inhibition of microRNA- and siRNA-induced RNA silencing," RNA, vol. 10 (3):544-550 (2004).
Meister, Gunter et al., "Human Argonaute2 Mediates RNA Cleavage Targeted by miRNAs and siRNAs," Molecular Cell, vol. 15:185-197 (2004).
Merriam-Webster Online Dictionary, "Pharmaceutical," http://www.merriam-webster.com/dictionary/pharmaceutical (2008).
Merriam-Webster online, "engineer," retrieved online at http://www.merriam-webster.com/dictonary (2008).
Molecular Biology of the Cell, Fourth Edition, "DNA Replication Mechanisms," retrieved online at http://www.ncbi.nlm.nih.gov/books/bv.fcgi?highlight=DNA&rid=mboc4.section.754 (2008).
Molecular Biology of the Cell, Fourth Edition, "Figure 4-4," retrieved online at http://www.ncbi.nlm.nih.gov/books/bv.fcgi?rid=mboc4.figgrp (2008).
Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section165 (2008).
Molecular Biology of the Cell, Fourth Edition, "Wobble base-pairing between codons and anticodons," retrieved online at http://www.ncbi.nlm.nih.gov/books/bv.fcgi?highlight=inosine&rid=mboc4.figgrp.1058 (2008).
Moss, Eric G. et al., "The Cold Shock Domain Protein LIN-28 Controls Developmental Timing in C. elegans and is Regulated by the lin-4 RNA," Cell, vol. 88:637-646 (1997).
Mourelatos, Zissimos et al., "miRNPs: a novel class of ribonucleoproteins containing numerous microRNAs," Genes & Development, vol. 16:720-728 (2002).
Mourrain, Philippe et al., "Arabidopsis SGS2 and SGS3 Genes are Required for Posttranscriptional Gene Silencing and Natural Virus Resistance," Cell, vol. 101:533-542 (2000).
Murchison, E.P. et al., "miRNAs on the move: miRNA biogenesis and the RNAi machinery," Curr. Opin. Cell. Biol., vol. 16(3):223-229 (2004).
Nykanen, A. et al., "ATP requirements and small interfering RNA structure in the RNA interference pathway," Cell, vol. 107(3):309-321 (2001).
Ohnishi, Yusuke et al, "Influence of assembly of siRNA elements into Rna-induced silencing complex by fork-siRNA duplex carrying nucleotide mismatches at the 3'- or 5'-end of the sense-stranded siRNA element," Biochemical and Biophysical Research Communications, vol. 329:516-521 (2005).
Olsen, Philip H. et al., "The lin-4 Regulatory RNA Controls Developmental Timing in Caenorhabditis elegans by Blocking LIN-14 Protein Synthesis after the Initiation of Translation," Developmental Biology, vol. 216:671-680 (1999).
Opalinska, Joanna B. et al., "Nucleic Acid Therapeutics for Hematologic Malignancies—Theoretical Considerations," Ann. N. Y. Acad. Sci., vol. 1082:124-136 (2006).
Opalinska, Joanna B. et al., "Nucleic-Acid Therapeutics: Basic Principles and Recent Applications," Nature Reviews Drug Discovery, vol. 1:503-514 (2002).
Elbashir, Sayda M. et al., "RNA interference is mediated by 21- and 22-nucleotide RNAs," Genes & Development, vol. 15:188-200 (2001).
Enright, Anton J. et al., "MicroRNA targets in *Drosophila*," Genome Biology, vol. 5:R1.1-R1.14 (2003).
Fagard, Mathilde et al., "AG01, QDE-2, and RDE-1 are related proteins required for post-transcriptional gene silencing in plants, quelling ni fungi, and RNA interference in animals," PNAS, vol. 97(21):11650-11654 (2000).
Filipowicz, Witold, "RNAi: The Nuts and Bolts of the RISC Machine," Cell, vol. 122:17-20 (2005).

Fire, Andrew et al., "Potent and specific genetic interference by double-stranded RNA in Caenorhabditis elegans," Nature, vol. 391:806-811 (1998).
Forstemann, Klaus et al., "*Drosophila* microRNAs are Sorted into Functionally Distinct Argonaute Complexes after Production by Dicer-1," Cell, vol. 130:287-297 (2007).
GenBank AC AAA37498, cyclophilin (*Mus musculus*), 1 page dated Apr. 27, 1993.
GenBank AC AAA52150, cyclophilin B (*Homo sapiens*), 1 page, dated Nov. 2, 1994.
GenBank Accession No. AB451383, Goshima, N. et al., "Human Protein Factory: an infrastructure to convert the human transcriptome into the in vitro-expressed human proteome of versatile utility," 2 pages, (2008).
GenBank AC NM_001075495, Zimin, A.V. et al., "A whole-genome assembly of the domestic cow, Bos taurus," Genome Biol., vol. 10(4):R42 (2009), 3 pages, dated Aug. 16, 2011.
GenBank AC NM_17748, Fabrizio, P. et al., "The evolutionary conserved core design of the catalytic activation step of the yeast spliceosome," Mol. Cell, vol. 36(4):593-608 (2009), 3 pages, Dec. 18, 2011.
GenBank Accession No. NM-021033, Yaman, E. et al., "RasGEF1A and RasGEF1B are guinine nucleotide exchange factors that descriminate between Rap GTP-binding proteins and mediate Rap2-specific nucleotide exchange," FEBS J., vol. 276(16):4607-4616 (2009), 4 pages (2011).
GenBank AC XM_002272515, Predicted: Vitis vinifera phosphatidylinositide phosphatase SAC1-like (LOC100248745), mRNA, 3 pages, dated Dec. 7, 2011.
Gerwitz, Alan M. et al., "On future's doorstep: RNA interference and the pharmacopeia of tomorrow," The Journal of Clinical Investigation, vol. 117(12):3612-3614 (2007).
Gong, Delquin et al, "Picking a winner: new mechanistic insights into the design of effective siRNAs," Trends in Biotechnology, vol. 22(9):451-454 (2004).
Grimm, D. et al., "Therapeutic application of RNAi: is mRNA targeting finally ready for prime time?" The Journal of Clinical Investigation, vol. 117(12):3633-3641 (2007).
Grishok, Alla et al., "Genes and Mechanisms Related to RNA Interference Regulate Expression of the Small Temporal RNAs that Control C. elegans Developmental Timing," Cell, vol. 106:23-34 (2001).
Grishok, Alla et al., "Genetic Requirements for Inheritance of RNAi in C. elegans," Science, vol. 287:2494-2497 (2000).
Grishok, Alla et al., "RNAi (Nematodes Caenorhabditis elegans)," Advances in Genetics, vol. 46:339-360 (2002).
Grosjean, Henri J. et al., "On the physical basis for ambiguity in genetic coding interactions," Proc. Natl. Acad. Sci. USA, vol. 75(2):610-614 (1978).
Grzelinski, Marius et al, "Rna Interference-Mediated Gene Silencing of Pleiotrophin Through Polyethylenimine-Complexed Small Interfering RNAs In Vivo Exerts Antitumoral Effects in Glioblastoma Xenografts," Human Gene Therapy, 17:751-766 (2006).
Ha, Ilho et al., "A bulged lin-4/lin-14 RNA duplex is sufficient for Caenorhabditis elegans lin-14 temporal gradient formation," Genes & Development, vol. 10:3041-3050 (1996).
Haley, B. et al., "Kinetic analysis of the RNAi enzyme complex," Nat Struct Mol Biol., vol. 11(7):599-606 (2004).
Haley, Benjamin et al., "In vitro analysis of RNA interference in *Drosophila melanogaster*," Methods, vol. 30:330-336 (2003).
Hamada, Makiko et al., "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, vol. 12:301-309 (2002).
Hammond, Scott M. et al., "Argonaute2, a Link Between Genetic and Biochemical Analyses of RNAi," Science, vol. 293:1146-1150 (2001).
Hammond, Scott M. et al., "Post-Transcriptional Gene Silencing by Double-Stranded RNA," Nature, vol. 2:110-119 (2001).
Hannon, Gregory J. et al., "Unlocking the potential of the human genome with RNA interference," Nature, vol. 431:371-378 (2004).

(56) References Cited

OTHER PUBLICATIONS

Harborth, Jens et al., "Sequence, Chemical, and Structural Variation of Small Interfering RNAs and Short Hairpin RNAs and the Effect on Mammalian Gene Silencing," Antisense and Nucleic Acid Drug Development, vol. 13:83-105 (2003).
Heale, Bret S.E. et al., "siRNA target site secondary structure predictions using local stable substructures," Nucleic Acids Research, vol. 33(3):1-10 (2005).
Hohjoh, Hirohiko et al., "RNA interference (RNAi) induction with various types of synthetic oligonucleotide duplexes in cultured human cells," FEBS Letters, vol. 521:195-199 (2002).
Hohjoh, Hirohiko, "Enhancement of RNAi activity by improved siRNA duplexes," FEBS Letters, vol. 557:193-198 (2004).
Holen, T. et al., "Similar behaviour of single-strand and double-strand siRNAs suggests they act through a common RNAi pathway," Nucleic Acids Res., vol. 31(9):2401-2407 (2003).
Holen, Torgeir et al., "Positional effects of short interfering RNAs targeting the human coagulation trigger Tissue Factor," Nucleic Acids Research, vol. 30(8):1757-1766 (2002).
Holen, Torgeir et al., "Tolerated wobble mutations in siRNAs decrease specificity, but can enhance activity in vivo," Nucleic Acids Research, vol. 33(15):4704-4710 (2005).
Hu-Lieskovan, Siwen et al, "Sequence-Specific Knockdown of EWS-FLI1 by Targeted, Nonrival Delivery of Small Interfering RNA Inhibits Tumor Growth in a Murine Model of Metastatic Ewing's Sarcoma," Cancer Research, 65:(19) 8984-8992 (2005).
Hutvágner, György et al., "A Cellular Function for the RNA-Interference Enzyme Dicer in the Maturation of the let-7 Small Temporal RNA," Science, vol. 293:834-838 (2001).
Hutvágner, György et al., "A microRNA in a Multiple-Turnover RNAi Enzyme Complex," Science, vol. 297:2056-2060 (2002).
Irie, Naoki et al., "Subtype- and species-specific knockdown of PKC using short interfering RNA," Biochemical and Biophysical Communications, vol. 298:738-743 (2002).
Jackson, A.L. et al., "Expression profiling reveals off-target gene regulation by RNAi," Nat. Biotechnol., vol. 21 (6):635-7 (2003).
Ketting, R.F. et al., "Dicer functions in RNA interference and in synthesis of small RNA involved in developmental timing in C. elegans," Genes Dev., vol. 15(20):2654-2659 (2001).
Ketting, René F. et a., "A genetic link between co-suppression and RNA interference ni C. elegans," Nature, vol. 404:296-298 (2000).
Ketting, René F. et a., "mut-7 of C. elegans, Required for Transposon Silencing and RNA Interference, Is a Homolog of Werner Syndrome Helicase and RNaseD," Cell, vol. 99:133-141 (1999).
Khvorova, A. et al., "Functional siRNAs and miRNAs exhibit strand bias," Cell, vol. 115(2):209-216 (2003).
Kierzek, Ryszard et al., "Thermodynamics of Single Mismatches in RNA Duplexes," Biochemistry, vol. 38:14214-14223 (1999).
Kim, Daniel H. et al., "Strategies for silencing human disease using RNA interference," Nature Reviews Genetics, vol. 8:173-184 (2007).
Kim, Dong-Ho et al., "Synthetic dsRNA Dicer substrates enhances RNAi potency and efficacy," Nature Biotechnology, vol. 23(2):222-226 (2005).
Kini, Hemant K. et al., "Effect of siRNA terminal mismatches on TRBP and Dicer binding and silencing efficiacy," FEBS Journal, vol. 276:6576-6585 (2009).
Knight, Scott W. et al., "A Role for the RNase III Enzyme DCR-1 in RNA Interference and Germ Line Development in Caenorhabditis elegans," Science, vol. 293:2269-2271 (2001).
Krol, J. et al., "Structural Features of MicroRNA (miRNA) Precursors and Their Relevance to miRNA Biogenesis and Small Interfering RNA/Short Hairpin RNA Design," J. Biol. Chem., vol. 279(40):42230-42239 (2004).
Akhtar, S. et al., "Nonviral delivery of synthetic siRNAs in vivo," The Journal of Clinical Investigation, vol. 117(12):3623-3632 (2007).
Amarzguioui, Mohammed et al., "Rational design and in vitro and in vivo delivery of Dicer substrate siRNA," Nature Protocols, vol. 1(2):508-517 (2006).
Amarzguioui, Mohammed et al., "Tolerance for mutations and chemical modifications in a siRNA," Nucleic Acids Research, vol. 31(2):589-595 (2003).
Ambros, Victor et al., "MicroRNAs and Other Tiny Endogenous RNAs in C. elegans," Current Biology, vol. 13:807-818 (2003).
Ameres et al., "Molecular basis for target RNA recognition and cleavage by human RISC," Cell, 130: 101-112 (2007).
Aravin, Alexei A. et al., "The Small RNA Profile during *Drosophila melanogaster* Development," Development Cell, vol. 5:337-350 (2003).
Bailly, Christian et al., "The use of diaminopurine to investigate structural properties of nucleic acids and molecular recognition between ligands and DNA," Nucleic Acids Research, vol. 26(19):4309-4314 (1998).
Bartel, David P. et al., "Micromanagers of gene expression: the potentially widespread influence of metazoan microRNAs," Nature Reviews Genetics, vol. 5:396-400 (2004).
Bartel, D.P., "MicroRNAs: genomics, biogenesis, mechanism, and function," Cell, vol. 116(2):281-297 (2004).
Beclin, Christophe et al., "A Branched Pathway for Transgene-Induced RNA Silencing in Plants," Current Biology, vol. 12:684-688, (2002).
Bernstein, Emily et al., "Role for a bidentate ribonuclease in the initiation step of RNA interference," Nature, vol. 409:363-366 (2001).
Boden, D, et al., "Efficient gene transfer of HIV-1-specific short hairpin RNA into human lymphocytic cells using recombinant adeno-associated virus vectors," Mol. Ther, vol. 9(3):396-402 (2004).
Boden, D. et al., "Enhanced gene silencing of HIV-1 specific siRNA using microRNA designed hairpins," Nucleic Acids Res., vol. 32(3):1154-1158 (2004).
Boese, Queta et al., "Mechanistic Insights Aid Computational Short Interfering RNA Design," Methods in Enzymology, vol. 392:73-96 (2005).
Bonnet, E. et al., "Evidence that microRNA precursors, unlike other non-coding RNAs, have lower folding free energies than random sequences," Bioinformatics, vol. 20(17):2911-2917 (2004).
Boutla, Alexandra et al., "Development defects by antisense-mediated inactivation of micro-RNAs 2 and 13 in *Drosophila* and the identification of putative target genes," Nucleic Acids Research, vol. 31(17):4973-4980 (2003).
Boutla, Alexandra et al., "Short 5'-phosphorylated double-stranded RNAs induce RNA interference in *Drosophila*," Current Biology, vol. 11:1776-1780 (2001).
Brennecke, Julius et al., "Bantam Encodes a Developmentally Regulated microRNA that Controls Cell Proliferation and Regulates the Proapoptotic Gene hid in *Drosophila*," Cell, vol. 113:25-36 (2003).
Brennecke, Julius et al., "Principles of MicroRNA—Target Recognition," PLoS Biology, vol. 3(3):404-418 (2005).
Brennecke, Julius et al., "Towards a complete description of the microRNA complement of animal genomes," Genome Biology, vol. 4:228-228.3 (2003).
Bumcrot, David et al., "RNAi therapeutics: a potential new class of pharmaceutical drugs," Nature Chemical Biology, vol. 2(12):711-719 (2006).
Caccone, Adalgisa et al., "Calibration of the Change in Thermal Stability of DNA Duplexes and Degree of Base Air Pair Mismatch," Journal of Molecular Evolution, vol. 27:212-216 (1988).
Caplen, Natasha J. et al., "dsRNA-mediated gene silencing in the cultured *Drosophila* cells: a tissue culture model for the analysis of RNA interference," Gene, vol. 252:95-105 (2000).
Caplen, Natasha J. et al., "Specific inhibition of gene expression by small double-stranded RNAs in invertebrate and vertebrate systems," PNAS, vol. 98(17):9742-9747 (2001).
Carthew, Richard W., "Gene silencing by double-stranded RNA," Current Opinion in Cell Biology, vol. 13:244-248 (2001).
Catalanotto, Caterina et al., "Gene silencing in worms and fungi," Nature, vol. 404:245 (2000).

(56) References Cited

OTHER PUBLICATIONS

Catalanotto, Caterina et al., "Involvement of small RNAs and role of the qde genes in the gene silencing pathway in Neurospora," Genes & Development, vol. 16:790-795 (2002).
Caudy, Amy A. et al., "Fragile X-related protein and VIG associate with the RNA interference machinery," Genes & Development, vol. 16:2491-2496 (2002).
Chi, J.T. et al., "Genomewide view of gene silencing by small interfering RNAs," PNAS, vol. 100(11):6343-6346 (2003).
Chiu, Ya-Lin et al., "RNAi in Human Cells: Basic Structural and Functional Features of Small Interfering RNA," Molecular Cell, vol. 10:549-561 (2002).
Chiu, Ya-Lin et al., "siRNA function in RNAi: A chemical modification analysis," RNA, vol. 9:1034-1048 (2003).
Chuang, Chiou-Fen et al., "Specific and heritable genetic interference by double-stranded RNA in *Arabidopsis thaliana*," PNAS, vol. 97(9):4985-4990 (2000).
Cogoni, Carlo et al., "Gene silencing in Neurospora crassa requires a protein homologous to RNA-dependent RNA polymerase," Nature, vol. 399:166-168 (1999).
Cogoni, Carlo et al., "Isolation of quelling-defective (qde) mutants impaired in posttranscriptional transgene-induced gene silencing in Neurospora crassa," Proc. Natl. Acad. Sci. USA, vol. 94:10233-10238 (1997).
Cogoni, Carlo et al., "Posttranscriptional Gene Silencing in Neurospora by a RecQ DNA Helicase," Science, vol. 286:2342-2344 (1999).
Conte, Darryl Jr. et al., "RNA Interference in Caenorhabditis Elegans," Current Protocols in Molecular Biology, F.M. Asubel et al., eds., John Wiley & Sons, pp. 26.3.1-26.3.20 (2003).
Corey, David R. et al., "Chemical modification: the key to clinical application of RNA interference?" The Journal of Clinical Investigation, vol. 117(12):3615-3622 (2007).
Czauderna, Frank et al., "Structural variations and stabilising modifications of synthetic siRNAs in mammalian cells," Nucleic Acids Research, vol. 31(11):2705-2716 (2003).
Dalmay, Tamas et al., "An RNA-Dependent RNA Polymerase Gene in Arabidopsis is Required for Posttranscriptional Gene Silencing Mediated by a Transgene but Not by a Virus," Cell, vol. 101:543-553 (2000).
Dalmay, Tamas et al., "SDE3 encodes an RNA helicase required for posttranscriptional gene silencing in Arabidopsis," The EMBO Journal, vol. 20(8):2069-2077 (2001).
Dharmacon RNA Technologies. On-Target siRNA. Company Brochure (2003).
Dharmacon RNA Technologies. Products for RNA Interference. Company brochure (2003).
Didiano, Dominic et al., "Perfect seed pairing is not a generally reliable predictor for miRNA-target interactions," Nature Structural & Molecular Biology, vol. 13(9):849-851 (2006).
Doench, John G. et al., "siRNAs can function as miRNAs," Genes & Development, vol. 17:438-442 (2003).
Doench, John G. et al., "Specificity of microRNA target selection in translational repression," Genes & Development, vol. 18:504-511 (2004).
Dostie, Josee et al., "Numerous microRNPs in neuronal cells containing novel microRNAs," RNA, vol. 9:180-186 (2003).
Du, Quan et al, "A sytematic analysis of the silencing effects of an active siRNA at all single-nucleotide mismatched target sites," Nucleic Acids Research, vol. 33(5):1671-1677 (2005).
Elbashir, Sayda M. et al., "Analysis of gene function in somatic mammalian cells using small interfering RNAs," Methods, vol. 26:199-213 (2002).
Elbashir, Sayda M. et al., "Duplexes of 21-nucleotide RNAs mediated RNA interference in cultured mammalian cells," Nature, vol. 411:494-498 (2001).
Elbashir, Sayda M. et al., "Functional anatomy of siRNAs for mediating efficient RNAi in *Drosophila melanogaster* embryo lysate," The EMBO Journal, vol. 20(23):6877-6888 (2001).
U.S. Appl. No. 13/917,480, filed Jun. 13, 2013, Zamore, Phillip D.

U.S. Appl. No. 13/654,199, filed Nov. 21, 2013, Zamore, Phillip D.
U.S. Appl. No. 14/294,817, filed Jun. 3, 2014, Zamore, Phillip D.
Tabara, Hiroaki et al., "The dsRNA Binding Protein RDE-4 Interacts with RDE-1, DCR-1, and a DExH-Box Helicase to Direct RNAi in C. elegans," Cell, vol. 109:861-871 (2002).
Tabara, Hiroaki et al., "The rde-1 Gene, RNA Interference and Transposon Silencing in C. elegans," Cell, vol. 99:123-132 (1999).
Tan P. H. et al, "Gene Knockdown with Intrathecal siRNA of NMDA Receptor NR2B Subunit Reduces Formalin-induced Nociception in the Rat," Gene Therapy, vol. 12, 59-66 (2005).
Tang, G. et al., "Biochemical dissection of RNA silencing in plants," Methods Mol. Biol., vol. 257:223-244 (2004).
Tang, Guiliang et al., "A biochemical framework for RNA silencing in plants," Genes & Development, vol. 17:49-63 (2003).
Thakker, Deepak R. et al, "Neurochemical and Behavioral Consequences of Widespred Gene Knockdown in the Adult Mouse Brain by Using Nonrival Interference," PNAS, vol. 101:49, 17270-17275 (2004).
Tijsterman, Marcel et al., "PPW-1, a PAZ/PIWI Protein Required for Efficient Germline RNAi, is Defective in a Natural Isolate of C. elegans," Current Biology, vol. 12:1535-1540 (2002).
Tijsterman, Marcel et al., "RNA Helicase MUT-14-Dependent Gene Silencing Triggered in C. elegans by Short Antisense RNAs," Science, Vo. 295:694-697 (2002).
Tomari, Y. et al., "RISC assembly defects in the *Drosophila* RNAi mutant armitage," Cell, vol. 116(6):831-841 (2004).
Tomari, Yukihide et al., "Perspective: machines for RNAi," Genes & Development, vol. 19:517-529 (2005).
Tuschl, Thomas et al., "siRNAs and miRNAs," Keystone Symposia, Abstract Book (2004).
Tuschl, Thomas et al., "Targeted mRNA degradation by double-stranded RNA in vitro," Genes & Development, vol. 13:3191-3197 (1999).
Valencia-Sanchez, Marco Antonio et al., "Control of translation and mRNA degradation by miRNAs and siRNAs," Genes & Development, vol. 20:515-524 (2006).
Vargason, Jeffrey M. et al., "Size selective recognition of siRNA by an RNA silencing suppressor," Cell, vol. 115:799-811 (2003).
Vaucheret, Herve et al., "Post-transcriptional gene silencing in plants," Journal of Cell Science, vol. 114:3083-3091, (2001).
Vella, Monica C. et al., "The C. elegans microRNA let-7 binds to imperfect let-7 complementary sites from the lin-41 3'UTR," Genes & Development, vol. 18:132-137 (2004).
Wang, J. et al., "Fas siRNA Reduces Apoptotic Cell Death of Allogeneic-Transplanted Hepatocytes in Mouse Spleen," Transplantation Proceedings, Vo. 35:1594-1595 (2003).
Waterhouse, Peter M. et al., "Gene silencing as an adaptive defense against viruses," Nature, vol. 411:834-842, (2001).
Wightman, Bruce et al., "Posttranscriptional Regulation of the Heterochronic Gene lin-14 by lin-4 Mediates Temporal Pattern Formation in C. elegans," Cell, vol. 75:855-862 (1993).
Wu-Sharf, Dancia et al., "Transgene and Transposon Silencing in Chlamydomonas reinhardtii by a DEAH-Box RNA Helicase," Science, vol. 290:1159-1162 (2000).
Xia, Haibin et al., "siRNA-mediated gene silencing in vitro and in vivo," Nature Biotechnology, vol. 20:1006-1010 (2002).
Xie, Zhixin et al., "Negative Feedback Regulation of Dicer-Like1 in Arabidopsis by microRNA-Guided mRNA Degradation," Current Biology, vol. 13:784-789 (2003).
Xu, Li et al., "Factors Affecting Long-Term Stability of Moloney Murine Leukemia Virus-Based Vectors," Virology, vol. 171:331-341 (1989).
Xu, Peizhang et al., "The *Drosophila* MicroRNA Mir-14 Suppresses Cell Death and Is Required for Normal Fat Metabolism," Current Biology, vol. 13:790-795 (2003).
Yi, Rui et al., "Exportin-5 mediates the nuclear export of pre-microRNAs and short hairpin RNAs," Genes & Development, vol. 17:3011-3016 (2003).
Yuan, Yu-Ren et al., "Crystal Structure of A. aeolicus Argonaute, a Site-Specific DNA-Guided Endoribonuclease, Provides Insights into RISC-Mediated mRNA Cleavage," Molecular Cell, vol. 19:405-419 (2005).

(56) References Cited

OTHER PUBLICATIONS

Zamore, Phillip D. et al., "RNAi: Double-Stranded RNA Directs the ATP-Dependent Cleavage of mRNA at 21 to 23 Nucleotide Intervals," Cell, vol. 101:25-33 (2000).
Zamore, Phillip D. et al., "siRNAs knock down hepatitis," Nature Medicine, vol. 9(3):266-267 (2003).
Zeng, Yan et al., "Both Natural and Designed Micro RNAs Can Inhibit the Expression of Cognate mRNAs When Expressed in Human Cells," Molecular Cell, vol. 9:1327-1333 (2002).
Zeng, Yan et al., "MicroRNAs and small interfering RNAs can inhibit mRNA expression by similar mechanisms," PNAS, vol. 100(17):9779-9784 (2003).
Zeng, Yan et al., "Sequence requirements for micro RNA processing and function in human cells," RNA, vol. 9:112-123 (2003).
Zhang, Haidi et al., "Human Dicer preferentially cleaves dsRNAs at their termini without a requirement for ATP," The EMBO Journal, vol. 21(21):5875-5885 (2002).
Zhang, Yingjie et al, "Engineering Mucosal RNA Interference in Vivo," Molecular Therapy, vol. 14:3, 336-342 (2006).
Zimmermann, Tracy S. et al, "RNAi-mediated Gene Silencing in Non-human Primates," Nature, vol. 441, 111-114 (2006).
Australian Office Action for Application No. 2010202861, 3 pages, dated Feb. 8, 2012.
Australian Office Action for Application No. 2010202861, dated Aug. 5, 2011.
Canadian Office Action for Application No. 2,528,012, dated Feb. 23, 2011.
European Search Report for Application No. 04753972.1, dated Oct. 31, 2006.
Further Facts and Evidence in support of Notice of Opposition to a European patent, Alnylarn Pharmaceuticals, Inc., Application No. EP 04 753 972.1, dated Jul. 20, 2011.
International Preliminary Report on Patentability for Application No. PCT/US2004/017130, dated Dec. 8, 2005.
International Search Report for Application No. PCT/US2005/029011, 4 pages, dated Apr. 13, 2006.
Invitation to Pay Additional Fees for Application No. PCT/US04/17130, dated Apr. 1, 2005.
Invitation to Pay Additional Fees for Application No. PCT/US2005/029011, 5 pages, dated Feb. 20, 2006.
Notice of opposition to a European patent, Alcon Research Ltd., Application No. EP 04 753 972.1, dated Jul. 20, 2011.
Notice of opposition to a European patent, Alnylam Pharmaceuticals, Inc., Application No. EP 04 753 972.1, dated Oct. 20, 2010.
Notice of opposition to a European patent, Alnylam Pharmaceuticals, Inc., Application No. EP 04 753 972.1, dated Oct. 29, 2010.
Notice of opposition to a European patent, Novartis AG, Application No. EP 04 753 972.1, dated Jul. 20, 2011.
Request for Ex Parte Reexamination Transmittal Form for U.S. Pat. No. 7,459,547, pp. 1-337, dated Jul. 30, 2010.
Request for Ex Parte Reexamination Transmittal Form for U.S. Pat. No. 7,732,593, pp. 1-344, dated Aug. 2, 2010.
Request for Ex Parte Reexamination Transmittal Form for U.S. Pat. No. 7,750,144, pp. 1-220, dated Jul. 30, 2010.

* cited by examiner

Fig. 3-1

Blunt-ended siRNAs against WSpET SOD sense

1
```
       5´ GAGACUUGGGCAAUGUGAC  3´  (SEQ ID NO.: 7)    (19.31)
          ..............................
       3´ TTCUCUGAACCCGUUACACUG 5´  (SEQ ID NO.: 8)   (SODp11.40)
(wT) 5´ GAUGAAGAGAGGCAUGUUGGAGACUUGGGCAAUGUGACUGCUGACAAAGAUGGU 3´ (SEQ ID NO.: 9)
```

2
```
       5´ GAGACUUGGGCAAUGUGAC  3´  (SEQ ID NO.: 7)    (19.31)
          ..............................
       3´ TTCUCUGAACCCGUUACACUU 5´  (SEQ ID NO.: 10)  (21.232)
(wT) 5´ GAUGAAGAGAGGCAUGUUGGAGACUUGGGCAAUGUGACUGCUGACAAAGAUGGU 3´ (SEQ ID NO.: 9)
```

3
```
       5´ GAGACUUGGGCAAUGUGAC  3´  (SEQ ID NO.: 7)    (19.31)
          ..............................
       3´ TTCUCUGAACCCGUUACACUI 5´  (SEQ ID NO.: 11)  (21.246)
(wT) 5´ GAUGAAGAGAGGCAUGUUGGAGACUUGGGCAAUGUGACUGCUGACAAAGAUGGU 3 (SEQ ID NO.: 9)
```

4
```
       5´ GAGACUUGGGCAAUGUGAC  3´  (SEQ ID NO.: 7)    (19.31)
          ..............................
       3´ TTAUCUGAACCCGUUACACUG 5´  (SEQ ID NO.: 12)  (21.252)
(wT) 5´ GAUGAAGAGAGGCAUGUUGGAGACUUGGGCAAUGUGACUGCUGACAAAGAUGGU 3´ (SEQ ID NO.: 9)
```

5
```
       5´ GAGACUUGGGCAAUGUGAA  3´  (SEQ ID NO.: 13)   (19.32)
          ..............................
       3´ TTCUCUGAACCCGUUACACUG 5´  (SEQ ID NO.: 8)   (SODp11.40)
(wT) 5´ GAUGAAGAGAGGCAUGUUGGAGACUUGGGCAAUGUGACUGCUGACAAAGAUGGU 3´ (SEQ ID NO.: 9)
```

6
```
       5´ GAGACUUGGGCAAUGUGAA  3´  (SEQ ID NO.: 13)   (19.32)
          ..............................
       3´ TTCUCUGAACCCGUUACACUU 5´  (SEQ ID NO.: 10)  (21.232)
(wT) 5´ GAUGAAGAGAGGCAUGUUGGAGACUUGGGCAAUGUGACUGCUGACAAAGAUGGU 3´ (SEQ ID NO.: 9)
```

7
```
       5´ GAGACUUGGGCAAUGUGAA  3´  (SEQ ID NO.: 13)   (19.32)
          ..............................
       3´ TTCUCUGAACCCGUUACACUI 5´  (SEQ ID NO.: 11)  (21.246)
(wT) 5´ GAUGAAGAGAGGCAUGUUGGAGACUUGGGCAAUGUGACUGCUGACAAAGAUGGU 3´ (SEQ ID NO.: 9)
```

Fig. 3-2

8
5´ GAGACUUGGGCAAUGUGAA 3´ (SEQ ID NO.: 13) (19.32)
3´ TTAUCUGAACCCGUUACACUG 5´ (SEQ ID NO.: 12) (21.252)
(wT) 5´ GAUGAAGAGAGGCAUGUUGGAGACUUGGGCAAUGUGACUGCUGACAAAGAUGGU 3´ (SEQ ID NO.: 9)

9
5´ GAGACUUGGGCAAUGUGACTT 3´ (SEQ ID NO.: 14) (SODp11.39)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

10
5´ UAGACUUGGGCAAUGUGACTT 3´ (SEQ ID NO.: 16) (21.251)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

11
5´ TAGACUUGGGCAAUGUGACTT 3´ (SEQ ID NO.: 17) (21.245)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

12
5´ GAGACUUGGGCAAUGUGAATT 3´ (SEQ ID NO.: 18) (21.233)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

13
5´ GAGACUUGGGCAAUGUGAUTT 3´ (SEQ ID NO.: 19) (21.279)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

14
5´ GAGACUUGGGCAAUGUGACTT 3´ (SEQ ID NO.: 14) (SODp11.39)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

Fig. 3-3

15
5´ IAGACUUGGGCAAUGUGACTT 3´ (SEQ ID NO.: 17) (21.245)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

16
5´ GAGACUUGGGCAAUGUGAATT 3´ (SEQ ID NO.: 18) (21.233)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

17
5´ GAGACUUGGGCAAUGUGAUTT 3 (SEQ ID NO.: 19) (21.279)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

Blunt-ended siRNAs (both ends, 19 nts) against WSpET 500 sense

18
5´ GAGACUUGGGCAAUGUGAC 3´ (SEQ ID NO.: 7) (19.31)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

19
5´ GAGACUUGGGCAAUGUGAC 3´ (SEQ ID NO.: 7) (19.31)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

20
5´ GAGACUUGGGCAAUGUGAA 3´ (SEQ ID NO.: 13) (19.32)
3´ CUCUGAACCCGUUACACUG 5´ (SEQ ID NO.: 15) (19.33)
(wT) 5´ GAUGAAGAGAGGCAUGUUGGAGACUUGGGCAAUGUGACUGCUGACAAAGAUGGU 3´ (SEQ ID NO.: 9)

21
5´ GAGACUUGGGCAAUGUGAA 3´ (SEQ ID NO.: 13) (19.32)
3´ AUCUGAACCCGUUACACUG 5´ (SEQ ID NO.: 20) (19.34)
(wT) 5´ GAUGAAGAGAGGCAUGUUGGAGACUUGGGCAAUGUGACUGCUGACAAAGAUGGU 3´ (SEQ ID NO.: 9)

Fig. 3-4

Blunt-ended siRNAs against WSpET SOD anti-sense

| 22 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAC 3´ (SEQ ID NO.: 7)  (19.31) |
| | 3´ TTCUCUGAACCCGUUACACUG 5´ (SEQ ID NO.: 8)  (SODp11.40) |

| 23 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAC 3´ (SEQ ID NO.: 7)  (19.31) |
| | 3´ TTCUCUGAACCCGUUACACUU 5´ (SEQ ID NO.: 10)  (21.232) |

| 24 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAC 3´ (SEQ ID NO.: 7)  (19.31) |
| | 3´ TTCUCUGAACCCGUUACACUI 5´ (SEQ ID NO.: 11)  (21.246) |

| 25 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAC 3´ (SEQ ID NO.: 7)  (19.31) |
| | 3´ TTAUCUGAACCCGUUACACUG 5´ (SEQ ID NO.: 12)  (21.252) |

| 26 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAA 3´ (SEQ ID NO.: 13)  (19.32) |
| | 3´ TTCUCUGAACCCGUUACACUG 5´ (SEQ ID NO.: 8)  (SODp11.40) |

| 27 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAA 3´ (SEQ ID NO.: 13)  (19.32) |
| | 3´ TTCUCUGAACCCGUUACACUU 5´ (SEQ ID NO.: 10)  (21.232) |

| 28 | (wT) 3´ CUACUUCUCUCCGUACAACCUCUGAACCCGUUACACUGACGACUGUUUCUACCA 5´ (SEQ ID NO.: 21) |
| | 5´ GAGACUUGGGCAAUGUGAA 3´ (SEQ ID NO.: 13)  (19.32) |
| | 3´ TTCUCUGAACCCGUUACACUI 5´ (SEQ ID NO.: 11)  (21.246) |

Fig. 3-5

29
(wT) 3´ CUACUUCUCUCCGUACAACCUCUGAACCCGUUACACUGACGACUGUUUCUACCA 5´ (SEQ ID NO.: 21)
         5´ GAGACUUGGGCAAUGUGAA 3´ (SEQ ID NO.: 13) (19.32)
              3´ TTAUCUGAACCCGUUACACUG 5´ (SEQ ID NO.: 12) (21.252)

30
(wT) 3´ CUACUUCUCUCCGUACAACCUCUGAACCCGUUACACUGACGACUGUUUCUACCA 5´ (SEQ ID NO.: 21)
         5´ GAGACUUGGGCAAUGUGACTT 3´ (SEQ ID NO.: 14) (SODp11.39)
              3´   CUCUGAACCCGUUACACUG 5´ (SEQ ID NO.: 15) (19.33)

31
(wT) 3´ CUACUUCUCUCCGUACAACCUCUGAACCCGUUACACUGACGACUGUUUCUACCA 5´ (SEQ ID NO.: 21)
         5´ UAGACUUGGGCAAUGUGACTT 3´ (SEQ ID NO.: 16) (21.251)
              3´   CUCUGAACCCGUUACACUG 5´ (SEQ ID NO.: 15) (19.33)

32
(wT) 3´ CUACUUCUCUCCGUACAACCUCUGAACCCGUUACACUGACGACUGUUUCUACCA 5´ (SEQ ID NO.: 21)
         5´ IAGACUUGGGCAAUGUGACTT 3´ (SEQ ID NO.: 17) (21.245)
              3´   CUCUGAACCCGUUACACUG 5´ (SEQ ID NO.: 15) (19.33)

33
(wT) 3´ CUACUUCUCUCCGUACAACCUCUGAACCCGUUACACUGACGACUGUUUCUACCA 5´ (SEQ ID NO.: 21)
         5´ GAGACUUGGGCAAUGUGAATT 3´ (SEQ ID NO.: 18) (21.233)
              3´   CUCUGAACCCGUUACACUG 5´ (SEQ ID NO.: 15) (19.33)

34
(wT) 3´ CUACUUCUCUCCGUACAACCUCUGAACCCGUUACACUGAGGACUGUUUCUACCA 5´ (SEQ ID NO.: 21)
         5´ GAGACUUGGGCAAUGUGAUTT 3´ (SEQ ID NO.: 19) (21.279)
              3´   CUCUGAACCCGUUACACUG 5´ (SEQ ID NO.: 15) (19.33)

35
(wT) 3´ CUACUUCUCUCCGUACAACCUCUGAACCCGUUACACUGACGACUGUUUCUACCA 5´ (SEQ ID NO.: 21)
         5´ GAGACUUGGGCAAUGUGACTT 3´ (SEQ ID NO.: 14) (SODp11.39)
              3´   AUCUGAACCCGUUACACUG 5´ (SEQ ID NO.: 20) (19.34)

Fig. 3-6

36 (wT) 3´ CUACUUCUCUCCGUACAACCUCUGAACCCGUUACACUGACGACUGUUUCUACCA 5´ (SEQ ID NO.: 21)
5´ UAGACUUGGGCAAUGUGACTT 3´ (SEQ ID NO.: 16) (21.251)
3´ AUCUGAACCCGUUACACUG 5´ (SEQ ID NO.: 20) (19.34)

37 (wT) 3´ CUACUUCUCUCCGUACAACCUCUGAACCCGUUACACUGACGACUGUUUCUACCA 5´ (SEQ ID NO.: 21)
5´ IAGACUUGGGCAAUGUGACTT 3´ (SEQ ID NO.: 17) (21.245)
3´ AUCUGAACCCGUUACACUG 5´ (SEQ ID NO.: 20) (19.34)

38 (wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAATT 3´ (SEQ ID NO.: 18) (21.233)
3´ AUCUGAACCCGUUACACUG 5´ (SEQ ID NO.: 20) (19.34)

39 (wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAUTT 3´ (SEQ ID NO.: 19) (21.279)
3´ AUCUGAACCCGUUACACUG 5´ (SEQ ID NO.: 20) (19.34)

Fig. 3-7

Blunt-ended siRNAs (both ends, 19 nts) against WSpET SOD anti-sense

40
(wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAC 3´ (SEQ ID NO.: 7) (19.31)
3´ CUCUGAACCCGUUACACUG 5´ (SEQ ID NO.: 15) (19.33)

41
(wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAC 3´ (SEQ ID NO.: 7) (19.31)
3´ AUCUGAACCCGUUACACUG 5´ (SEQ ID NO.: 20) (19.34)

42
(wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAA 3´ (SEQ ID NO.: 13) (19.32)
3´ CUCUGAACCCGUUACACUG 5´ (SEQ ID NO.: 15) (19.33)

43
(wT) 3´ CUACUUCUCUCCGUACAACCUCUGAACCCGUUACACUGACGACUGUUUCUACCA 5´ (SEQ ID NO.: 21)
5´ GAGACUUGGGCAAUGUGAA 3´ (SEQ ID NO.: 13) (19.32)
3´ AUCUGAACCCGUUACACUG 5´ (SEQ ID NO.: 20) (19.34)

METHODS AND COMPOSITIONS FOR ENHANCING THE EFFICACY AND SPECIFICITY OF SINGLE AND DOUBLE BLUNT-ENDED SIRNA

RELATED APPLICATIONS

This application is a continuation of U.S. patent application Ser. No. 13/270,920, entitled "Methods and Compositions for Enhancing the Efficacy and Specificity of Single and Double Blunt-Ended siRNA", filed Oct. 11, 2011, which is a continuation of U.S. patent application Ser. No. 11/022,055, entitled "Methods and Compositions for Enhancing the Efficacy and Specificity of Single and Double Blunt-Ended siRNA", filed Dec. 22, 2004, which claims priority to U.S. Provisional Patent Application Ser. No. 60/532,116, entitled "Methods and Compositions for Enhancing the Efficacy and Specificity of Single and Double Blunt-Ended siRNA", filed Dec. 22, 2003. The entire contents of the above-referenced applications are incorporated herein by this reference.

RELATED INFORMATION

The contents of any patents, patent applications, and references cited throughout this specification are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 29, 2016, is named 559618-UMY-097CON2 SL.txt and is 6,684 bytes in size.

BACKGROUND OF THE INVENTION

Small interfering RNAs (siRNAs) are produced by the cleavage of double-stranded RNA (dsRNA) precursors by Dicer, a member of the RNase III family of dsRNA-specific endonucleases. Typically, siRNAs result when transposons, viruses, or endogenous genes express long dsRNA or when dsRNA is introduced experimentally into plant or animal cells to trigger gene silencing, a process known as RNA interference (RNAi).

siRNAs were first identified as the specificity determinants of the RNA interference (RNAi) pathway, where they act as guides to direct endonucleolytic cleavage of their target RNAs. Prototypical siRNA duplexes are 21 nucleotide, double-stranded RNAs that contain 19 base pairs, with two-nucleotide, 3' overhanging ends. Active siRNAs contain 5' phosphates and 3' hydroxyls.

siRNAs are typically found in the RNA-induced silencing complex (RISC) that mediates both cleavage and translational control. siRNA duplexes can assemble into RISC in the absence of target mRNA, both in vivo and in vitro. Each RISC contains only one of the two strands of the siRNA duplex. Since siRNA duplexes have no foreknowledge of which siRNA strand will guide target cleavage, both strands must assemble with the appropriate proteins to form a RISC.

It has been observed that both siRNA strands are competent to direct RNAi (Tuschl et al., *Genes Dev* 13, 3191-3197 (1999); Hammond et al., *Nature* 404, 293-296 (2000); Zamore et al., *Cell* 101, 25-33 (2000); Elbashir et al., *Genes Dev* 15, 188-200 (2001); Elbashir et al., *EMBO J.* 20, 6877-6888 (2001); Nykänen et al., *Cell* 107, 309-321 (2001). That is, the antisense strand of an siRNA can direct cleavage of a corresponding sense RNA target, whereas the sense siRNA strand directs cleavage of an antisense target. In this way, siRNA duplexes appear to be functionally symmetric.

The ability to control which strand of an siRNA duplex enters into the RISC complex to direct cleavage of a corresponding RNA target would provide a significant advance for both research and therapeutic applications of RNAi technology.

SUMMARY OF THE INVENTION

The invention solves the foregoing problems of siRNA gene targeting by determining the structural and functional characteristics of single and blunt-ended siRNAs and in particular, their strand specificity for a gene target. Accordingly, an entirely new constellation of single and double blunt-ended siRNA agents, e.g., siRNA duplexes, can be designed to efficiently and specifically modulate a sense and/or antisense gene target.

In addition, the invention provides a method for introducing alterations in either the 5', 3', or both the 5' and 3' of a single or double blunt-ended siRNA such that either the sense, the antisense, or both the sense and antisense strand will enter the RNAi pathway (e.g., RISC) and target a cognate gene target(s) for cleavage and destruction. Typically, the alteration takes the form of a mismatched base pair that allows for a portion of the siRNA duplex, e.g., the 5' end of the antisense strand, to separate or fray.

Accordingly, the invention has several advantages which include, but are not limited to, the following:
  providing methods for designing single and double blunt-ended siRNA agents, e.g., siRNA duplexes, have a characteristic strand specificity;
  providing single and double blunt-ended siRNA agents, e.g., siRNA duplexes or small hairpin RNAs (shRNAs) with at least one blunt end, suitable for gene modulation in plant or animal cells; and
  methods for modulating gene expression in a subject in need thereof using the single or double blunt-ended siRNA compositions of the invention, e.g., in the form of a pharmaceutical composition suitable for administering to a patient.

Accordingly, in one aspect, the invention provides methods for improving the efficiency (or specificity) of an RNAi reaction comprising modifying (e.g., increasing) the asymmetry of an RNAi agent (i.e., an RNA duplex having at least one blunt end) such that the ability of the sense or second strand to mediate RNAi (e.g., mediate cleavage of a target RNA) is lessened.

In one embodiment, the asymmetry is increased in favor of the 5' end of the first strand, e.g., by lessening the bond strength (e.g., the strength of the interaction) between the 5' end of the first strand and 3' end of the second strand relative to the bond strength (e.g., the strength of the interaction) between the 5' end of the second strand and the 3' end of the first strand.

In another embodiment, the asymmetry is increased in favor of the 5' end of the first strand by increasing bond strength (e.g., the strength of the interaction) between the 5' end of the second or sense strand and the 3' end of the first or antisense strand, relative to the bond strength (e.g., the strength of the interaction) between the 5' end of the first and the 3' end of the second strand.

In another embodiment, the bond strength is increased, e.g., the hydrogen bonding is increased between nucleotides or analogs at the 5' end, e.g., within 5 nucleotides of the second or sense strand (numbered from the 5' end of the second strand) and complementary nucleotides of the first or antisense strand. It is understood that the asymmetry can be zero (i.e., no asymmetry), for example, when the bonds or base pairs between the 5' and 3' terminal bases are of the same nature, strength or structure. More routinely, however, there exists some asymmetry due to the different nature, strength or structure of at least one nucleotide (often one or more nucleotides) between terminal nucleotides or nucleotide analogs.

Accordingly, in one aspect, the instant invention provides a method of enhancing the ability of a first strand of a single or double blunt-ended RNAi agent to act as a guide strand in mediating RNAi, involving lessening the base pair strength between the 5' end of the first strand and the 3' end of a second strand of the duplex as compared to the base pair strength between the 3' end of the first strand and the 5' end of the second strand.

In a related aspect, the invention provides a method of enhancing the efficacy of a single or double blunt-ended siRNA duplex, the siRNA duplex comprising a sense and an antisense strand, involving lessening the base pair strength between the antisense strand 5' end (AS 5') and the sense strand 3' end (S 3') as compared to the base pair strength between the antisense strand 3' end (AS 3') and the sense strand 5' end (S '5), such that efficacy is enhanced.

In another aspect of the invention, a method is provided for promoting entry of a desired strand of an single or double blunt-ended siRNA duplex into a RISC complex, comprising enhancing the asymmetry of the single or double blunt-ended siRNA duplex, such that entry of the desired strand is promoted. In one embodiment of this aspect of the invention, the asymmetry is enhanced by lessening the base pair strength between the 5' end of the desired strand and the 3' end of a complementary strand of the duplex as compared to the base pair strength between the 3' end of the desired strand and the 5' end of the complementary strand.

In another aspect of the invention, a single or double blunt-ended siRNA duplex is provided comprising a sense strand and an antisense strand, wherein the base pair strength between the antisense strand 5' end (AS 5') and the sense strand 3' end (S 3') is less than the base pair strength between the antisense strand 3' end (AS 3') and the sense strand 5' end (S '5), such that the antisense strand preferentially guides cleavage of a target mRNA.

In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand.

In another embodiment, the base pair strength is less due to at least one mismatched base pair between the 5' end of the first or antisense strand and the 3' end of the second or sense strand. Preferably, the mismatched or wobble base pair is selected from the group consisting of G:A, C:A, C:U, G:G, A:A, C:C, U:U, I:A, I:U, and I:C.

In yet another embodiment, the base pair strength is less due to at least one base pair comprising a modified nucleotide. In preferred embodiments, the modified nucleotide is selected from the group consisting of 2-amino-G (e.g., 2,2-diamino-1,2-dihydro-purin-6-one), 2-amino-A, 2,6-diamino-G, and 2,6-diamino-A.

In other embodiments of the above aspects, the single or double blunt-ended RNAi agent or siRNA duplex is derived from an engineered precursor, and can be chemically synthesized or enzymatically synthesized.

In another aspect of the instant invention, compositions are provided comprising a single or double blunt-ended siRNA duplex of the invention formulated to facilitate entry of the siRNA duplex into a cell. Also provided are pharmaceutical composition comprising a siRNA duplex of the invention.

Further provided are an engineered pre-miRNA comprising the siRNA duplex of any one of the preceding claims, as well as a vector encoding the pre-miRNA. In related aspects, the invention provides a pre-miRNA comprising the pre-miRNA, as well as a vector encoding the pre-miRNA.

Also featured in the instant invention are small hairpin RNA (shRNA) capable of forming at least a single blunt end comprising nucleotide sequence identical to the sense and antisense strand of the siRNA duplex as described above.

In one embodiment, the nucleotide sequence identical to the sense strand is upstream of the nucleotide sequence identical to the antisense strand. In another embodiment, the nucleotide sequence identical to the antisense strand is upstream of the nucleotide sequence identical to the sense strand. Further provided are vectors and transgenes encoding the shRNAs of the invention.

In yet another aspect, the invention provides cells comprising the vectors featured in the instant invention. Preferably, the cell is a mammalian cell, e.g., a human cell.

In other aspects of the invention, methods of enhancing silencing of a target mRNA, comprising contacting a cell having an RNAi pathway with any of the foregoing single or double blunt-ended RNAi agents such that silencing is enhanced.

Also provided are methods of enhancing silencing of a target mRNA in a subject, comprising administering to the subject a pharmaceutical composition comprising any of the foregoing single or double blunt-ended RNAi agents such that silencing is enhanced.

Further provided is a method of decreasing silencing of an inadvertent target mRNA by a single or double blunt-ended RNAi agents the RNAi agent comprising a sense strand and an antisense strand involving the steps of: (a) detecting a significant degree of complementarity between the sense strand and the inadvertent target; and (b) enhancing the base pair strength between the 5' end of the sense strand and the 3' end of the antisense strand relative to the base pair strength between the 3' end of the sense strand and the 5' end of the antisense strand; such that silencing of the inadvertent target mRNA is decreased. In a preferred embodiment, the silencing of the inadvertent target mRNA is decreased relative to silencing of a desired target mRNA.

Other features and advantages of the invention will be apparent from the following detailed description and claims.

BRIEF DESCRIPTION OF THE DRAWINGS

FIG. 3 shows the structure of all siRNA duplexes tested, in particular, the single and double blunt-ended siRNA duplexes of the invention and their correspondence with sense or antisense gene targets to determine their efficacy and specificity. Each siRNA duplex tested is identified by a number which corresponds to functional target specificity results obtained in vitro using *Drosophila* extracts (and shown in FIG. 5). Single blunt-ended siRNA duplexes and double blunted-ended siRNA duplexes and their alignment with sense targets are numbered, respectively, 1-17 and 18-21. The foregoing and their alignment with antisense targets are numbered, respectively, 22-43.

DETAILED DESCRIPTION OF THE INVENTION

Figure 1:
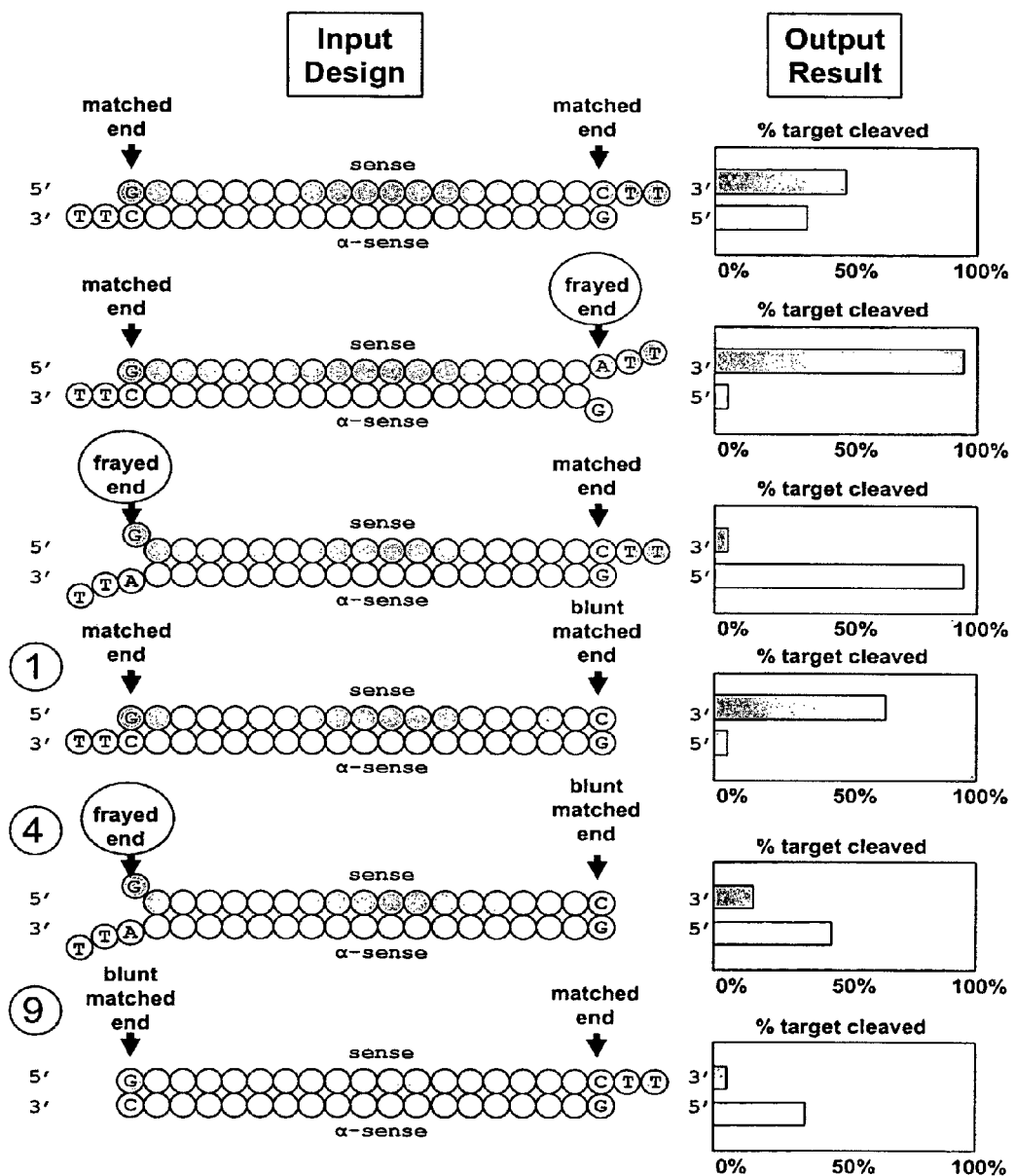
FIG. 1 shows a schematic of the structural and functional characteristics of classical siRNA (i.e., having 3' dinucleotide overhangs) with either a 5' or 3' frayed end as compared to the siRNAs of the invention having at least one blunt end. Selected single blunt-ended siRNAs with either a 5' or 3' frayed end are shown as well as their corresponding ability to target cleavage of a test sense and/or antisense target. Numbers on the left correspond to the siRNA shown in further detail structurally in FIG. 4 and as tested for target specificity in FIG. 5.

In order to provide a clear understanding of the specification and claims, the following definitions are conveniently provided below.
Definitions As used herein the term "blunt end", for example, "single blunt-end" or "double blunt-ended siRNA" refers to, e.g., an siRNA duplex where at least one end of the duplex lacks any overhang, e.g., a 3' dinucleotide overhang, such that both the 5' and 3' strand end together, i.e., are flush or as referred to herein, are blunt. The molecules of the invention have at least one blunt end and, preferably, two blunt ends, i.e., are double blunt-ended (See FIGS. 1-3 which show schematically classical siRNA duplexes having 3' dinucleotide overhangs as compared with the single and double blunt-ended siRNAs of the invention).

The term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, an siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). As mentioned above, at least one end if not both ends of the siRNA of the invention, is blunt. Preferred single blunt-ended siRNA molecules comprise a 21 nucleotide (nt) strand paired with a strand that is 19 nt, 18 nt, or 17 nt. In another embodiment, single blunt-ended siRNA molecules comprise a 19 nt strand paired with a 18 nt strand or, preferably, a 17 nt strand, wherein the 19 nt strand is favored to enter the RISC pathway. It is also understood that a blunt ended siRNA, if base paired or matched, is more prone to separating or fraying, then an end that is matched but also has a one or more nucleotide overhang, e.g., a dinucleotide overhang, because of the unpaired helical nature of the overhang and the stacking forces which contribute to maintaining the base pairs immediately downstream.

The term "RNA interference" ("RNAi") (also referred to in the art as "gene silencing" and/or "target silencing", e.g., "target mRNA silencing") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "antisense strand" of an siRNA or RNAi agent refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process.

The term "sense strand" or "second strand" of an siRNA or RNAi agent refers to a strand that is complementary to the antisense strand or first strand. Antisense and sense strands can also be referred to as first or second strands, the first or second strand having complementarity to the target sequence and the respective second or first strand having complementarity to said first or second strand.

The term "guide strand" refers to a strand of an RNAi agent, e.g., an antisense strand of an siRNA duplex, that enters into the RISC complex and directs cleavage of the target mRNA.

The term "target gene" is a gene whose expression is to be selectively inhibited or "silenced". This silencing is achieved by cleaving the mRNA of the target gene by an siRNA or miRNA, e.g., an siRNA or miRNA that is created from an engineered RNA precursor by a cell's RNAi system. One portion or segment of a duplex stem of the RNA precursor is an antisense strand that is complementary, e.g., sufficiently complementary to trigger the destruction of the desired target mRNA by the RNAi machinery or process, to a section of about 18 to about 40 or more nucleotides of the mRNA of the target gene.

The term "asymmetry", as in the asymmetry of a single or double blunt-ended siRNA duplex, refers to an inequality of bond strength or base pairing strength between the siRNA termini (e.g., between terminal nucleotides on a first strand and terminal nucleotides on an opposing second strand, e.g., a base pair mismatch that allows for a separation or fraying of the end(s)), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

The term "bond strength" or "base pair strength" refers to the strength of the interaction between pairs of nucleotides (or nucleotide analogs) on opposing strands of an oligonucleotide duplex (e.g., an siRNA duplex), due primarily to hydrogen-bonding, Van der Waals interactions, and the like between such nucleotides (or nucleotide analogs).

The term "fray" or "fraying" refers to the ability of a portion of the siRNA duplex of the invention to separate, typically at the end, preferably at the 5' end of the first or antisense strand, due to a base pair mismatch. For determining the thermodynamic stability or local thermodynamic stability of such ends, energy rules can be based on nearest neighbor analysis and/or amount of stacking.

DETAILED DESCRIPTION

Overview

The present invention features "small interfering RNA molecules" ("siRNA molecules" or "siRNA") having at least one blunt end, methods of making such siRNA molecules and methods for using the single or double blunt-ended siRNA molecules (e.g., research and/or therapeutic methods). A blunt-ended siRNA molecule of the invention is a duplex consisting of a sense strand and complementary antisense strand, the antisense strand having sufficient complementarity to a target mRNA to mediate RNAi and having at least one end (5', 3', or both 5' and 3') without an overhang. Accordingly, the molecules of the invention are distinguished from typical siRNA molecules which have a 3' dinucleotide overhang at each end of the molecule.

Preferably, the strands are aligned such that, at one end, preferably at both ends, there are no bases at the end of the strands which do not align (i.e., for which no complementary bases occur in the opposing strand) such that no overhang occurs at one or both ends of the duplex when the strands are annealed. Preferably, the single or double blunt-ended siRNA molecule has a length from about 10-50 or more nucleotides, i.e., each strand comprises 10-50 nucleotides (or nucleotide analogs). More preferably, the siRNA molecule has a length from about 15-45 or 15-30 nucleotides. Even more preferably, the siRNA molecule has a length from about 16-25 nucleotides, 18-23 nucleotides, or 19 nucleotides. The single or double blunt-ended siRNA molecules of the invention further have a sequence that is "sufficiently complementary" to a target mRNA sequence to direct target-specific RNA interference (RNAi), as defined herein, i.e., the single or double blunt-ended siRNA has a sequence sufficient to trigger the destruction of the target mRNA by the RNAi machinery or process.

1. Preferred RNA Molecules

The single or double blunt-ended siRNAs featured in the invention provide enhanced specificity and efficacy for mediating RISC-mediated cleavage of a desired target gene. In a preferred aspect, the base pair strength between the antisense strand 5' end (AS 5') and the sense strand 3' end (S 3') of the siRNAs is less than the bond strength or base pair strength between the antisense strand 3' end (AS 3') and the sense strand 5' end (S '5), such that the antisense strand preferentially guides cleavage of a target mRNA. In one embodiment, the bond strength or base-pair strength is less due to fewer G:C base pairs between the 5' end of the first or antisense strand and the 3' end of the second or sense strand than between the 3' end of the first or antisense strand and the 5' end of the second or sense strand.

In another embodiment, the bond strength or base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U. In a related embodiment, the bond strength or base pair strength is less due to at least one wobble base pair, e.g., G:U, between the 5' end of the first or antisense strand and the 3' end of the second or sense strand.

In yet another embodiment, the bond strength or base pair strength is less due to at least one base pair comprising a rare nucleotide, e.g., inosine (I). Preferably, the base pair is selected from the group consisting of an I:A, I:U, and I:C.

In yet another embodiment, the bond strength or base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

In general, single or double blunt-ended siRNAs containing nucleotide sequences sufficiently identical to a portion of the target gene to effect RISC-mediated cleavage of the target gene are preferred.

2. Gene Target Sequence Identity

Typically, 100% sequence identity between the single or double blunt-ended siRNA and the target gene is not required to practice the present invention. The invention has the advantage of being able to tolerate preferred sequence variations of the methods and compositions of the invention in order to enhance efficiency and specificity of RNAi. For example, single or double blunt-ended siRNA sequences with insertions, deletions, and single point mutations relative to the target sequence can also be effective for inhibition. Alternatively, single or double blunt-ended siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the siRNA antisense strand and the portion of the target gene is preferred. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)—(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

3. Other Modifications for RNA Stability

The RNA molecules of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features small interfering RNAs (siRNAs) that include a sense strand and an antisense strand, wherein the antisense strand has a sequence sufficiently complementary to a target mRNA sequence to direct target-specific RNA interference (RNAi) and wherein the sense strand and/or antisense strand is modified by the substitution of internal nucleotides with modified nucleotides, such that in vivo stability is enhanced as compared to a corresponding unmodified siRNA. As defined herein, an "internal" nucleotide is one occurring at any position other than the 5' end or 3' end of nucleic acid molecule, poly-nucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

4. RNA Synthesis

RNA may be produced enzymatically or by partial/total organic synthesis, any modified ribonucleotide can be introduced by in vitro enzymatic or organic synthesis. In one embodiment, an RNAi agent is prepared chemically. Methods of synthesizing RNA molecules are known in the art, in particular, the chemical synthesis methods as de scribed in Verma and Eckstein (1998) *Annul Rev. Biochem.* 67:99-134.

In another embodiment, a ss-siRNA is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies.

In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the siRNA can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In one embodiment, the single or double blunt-ended siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the ss-siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses ss-siRNA from a recombinant construct may be produced by introducing the construct into a zygote, an embryonic stem cell, or another multipotent cell derived from the appropriate organism.

5. Selecting a Gene Target

In one embodiment, the target mRNA of the invention encodes the amino acid sequence of a cellular protein, e.g., a protein involved in cell growth or suppression, e.g., a nuclear, cytoplasmic, transmembrane, membrane-associated protein, or cellular ligand. In another embodiment, the target mRNA of the invention specifies the amino acid sequence of an extracellular protein (e.g., an extracellular matrix protein or secreted protein). Typical classes of proteins are listed for illustrative purposes.

Developmental proteins suitable for targeting according to the invention include e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors).

Oncogene-encoded proteins suitable for targeting according to the invention include, e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES).

Tumor suppressor proteins suitable for targeting according to the invention include e.g., APC, BRCA1, BRCA2, MADH4, MCC, NF I, NF2, RB I, TP53, and WTI).

Enzymatic proteins suitable for targeting according to the invention include, e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectin-esterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, xylanases, and telomerases.

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

By modulating the expression of the foregoing proteins, valuable information regarding the function of such proteins and therapeutic benefits which may be obtained from such modulation can be obtained.

6. Assay for Testing Engineered RNA Precursors

*Drosophila* embryo lysates can be used to determine if the engineered siRNAs of the invention, e.g., single or double blunt-ended siRNA duplexes (but also, e.g., expressed shRNAs) have their intended function (see also Examples 1-3). This lysate assay is described in Tuschl et al., 1999, supra, Zamore et al., 2000, supra, and Hutvdgner et al., *Science* 293, 834-838 (2001). These lysates recapitulate RNAi in vitro, thus permitting investigation into, e.g., which strand enters the complex, is assembled into RISC, and is used as a guide strand for target destruction. Briefly, the test siRNA is incubated with *Drosophila* embryo lysate for various times, then assayed for the production of the mature siRNA by primer extension or Northern hybridization. As in the in vivo setting, mature RNA accumulates in the cell-free reaction. Thus, an RNA corresponding to the proposed precursor can be shown to be converted into a siRNA duplex in the *Drosophila* embryo lysate.

Furthermore, an engineered RNA precursor can be functionally tested in the *Drosophila* embryo lysates. In this case, the engineered RNA precursor is incubated in the lysate in the presence of a 5' radiolabeled target mRNA in a standard in vitro RNAi reaction for various lengths of time. The target mRNA can be 5' radiolabeled using guanylyl transferase (as described in Tuschl et al., 1999, supra and references therein) or other suitable methods. The products of the in vitro reaction are then isolated and analyzed on a denaturing acrylamide or agarose gel to determine if the target mRNA has been cleaved in response to the presence of the engineered RNA precursor in the reaction. The extent and position of such cleavage of the mRNA target will indicate if the engineering of the precursor created a pre-siRNA capable of mediating sequence-specific RNAi.

7. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals Alternatively, vectors, e.g., transgenes encoding a siRNA of the invention, i.e., having at least one blunt end, can be engineered into a host cell or transgenic animal using art recognized techniques.

8. Methods of Treatment:

The present invention provides for both prophylactic and therapeutic methods of treating a subject at risk of (or susceptible to) a disorder or having a disorder associated with aberrant or unwanted target gene expression or activity. It is understood that "treatment" or "treating" as used herein, is defined as the application or administration of a therapeutic agent (e.g., a RNAi agent or vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

9. Prophylactic Methods

In another aspect, the invention provides a method for preventing in a subject, a disease or condition associated with an aberrant or unwanted target gene expression or activity, by administering to the subject a therapeutic agent (e.g., a RNAi agent or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

10. Therapeutic Methods

In yet another aspect, the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., a RNAi agent or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

11. Pharmacogenomics

The therapeutic agents (e.g., a RNAi agent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266

12. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

13. Knockout and/or Knockdown Cells or Organisms

A further preferred use for the RNAi agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

14. Transgenic Organisms

Engineered RNA precursors of the invention can be expressed in transgenic animals. These animals represent a model system for the study of disorders that are caused by, or exacerbated by, overexpression or underexpression (as compared to wildtype or normal) of nucleic acids (and their encoded polypeptides) targeted for destruction by the RNAi agents, e.g., siRNAs and shRNAs, and for the development of therapeutic agents that modulate the expression or activity of nucleic acids or polypeptides targeted for destruction.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Invertebrates such as *Caenorhabditis elegans* or *Drosophila* can be used as well as non-mammalian vertebrates such as fish (e.g., zebrafish) or birds (e.g., chickens).

Engineered RNA precursors with stems of 18 to 30 nucleotides in length are preferred for use in mammals, such as mice. A transgenic founder animal can be identified based upon the presence of a transgene that encodes the new RNA precursors in its genome, and/or expression of the transgene in tissues or cells of the animals, for example, using PCR or Northern analysis. Expression is confirmed by a decrease in the expression (RNA or protein) of the target sequence.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci. USA 78:5016; Brinster et al., 1985, Proc. Natl. Acad. Sci. USA 82:4438). Alternatively, the transgene can be introduced into the pronucleus by retroviral infection. A detailed procedure for producing such transgenic mice has been described (see e.g., Hogan et al., *Manipulating the Mouse Embryo*. Cold Spring Harbor Laboratory, Cold Spring Harbor, N.Y. (1986); U.S. Pat. No. 5,175,383 (1992)). This procedure has also been adapted for other animal species (e.g., Hammer et al., 1985, *Nature* 315:680; Murray et al., 1989, *Reprod. Fert. Devl.* 1:147; Pursel et al., 1987, *Vet. Immunol. Histopath.* 17:303; Rexroad et al., 1990, J. Reprod. Fert. 41 (suppl): 1 19; Rexroad et al., 1989, *Molec. Reprod. Devl.* 1:164; Simons et al., 1988, BioTechnology 6:179; Vize et al., 1988, J. Cell. Sci. 90:295; and Wagner, 1989, J. Cell. Biochem. 13B (suppl): 164). Clones of the non-human transgenic animals described herein can be produced according to the methods described in Wilmut et al. ((1997) *Nature,* 385: 810-813) and PCT publication Nos. WO 97/07668 and WO 97/07669.

15. Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said so target protein, (b) at least one RNAi agent molecule capable of inhibiting the expression of said at least one endogenous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogenous target gene on the nucleic acid level such that the expression of the exogenous target nucleic acid is substantially less inhibited by the RNAi agent than the expression of the endogenous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222: 301-310); (Ladner supra.)).

In a preferred embodiment, the library is a natural product library, e.g., a library produced by a bacterial, fungal, or yeast culture. In another preferred embodiment, the library is a synthetic compound library.

This invention is further illustrated by the following examples which should not be construed as limiting.

EXEMPLIFICATION

Throughout the examples, the following materials and methods were used unless otherwise stated.

Materials and Methods

In general, the practice of the present invention employs, unless otherwise indicated, conventional techniques of nucleic acid chemistry, recombinant DNA technology, molecular biology, biochemistry, and cell and cell extract preparation. See, e.g., *DNA Cloning*, Vols. 1 and 2, (D. N. Glover, Ed. 1985); *Oligonucleotide Synthesis* (M. J. Gait, Ed. 1984); *Oxford Handbook of Nucleic Acid Structure*, Neidle, Ed., Oxford Univ Press (1999); *RNA Interference: The Nuts & Bolts of siRNA Technology*, by D. Engelke, DNA Press, (2003); *Gene Silencing by RNA Interference: Technology and Application*, by M. Sohail, CRC Press (2004); Sambrook, Fritsch and Maniatis, *Molecular Cloning*: Cold Spring Harbor Laboratory Press (1989); and Current Protocols in Molecular Biology, eds. Ausubel et al., John Wiley & Sons (1992). See also PCT/US03/24768; U.S. Ser. No. 60/475,331; U.S. Ser. No. 60/507,928; and U.S. Ser. No. 60/475,386, of which all are incorporated in their entireties by reference herein.

siRNA Preparation

Synthetic RNAs (Dharmacon) were deprotected according to the manufacturer's protocol. siRNA strands were annealed (Elbashir et al., Genes Dev 15, 188-200 (2001) and used at 50 nM final concentration unless otherwise noted. siRNA single strands were phosphorylated with polynucleotide kinase (New England Biolabs) and 1 mM ATP according to the manufacturer's directions and used at 500 nM final concentration.

Sense and Anti-Sense Target Preparation

Target RNAs were transcribed with recombinant, histidine-tagged, T7 RNA Polymerase from PCR products as described (Nykänen et al., 2001, supra; Hutvagner and Zamore, Science 297, 2056-2060 (2002), except for sense sod1 mRNA, which was transcribed from a plasmid template (Crow et al., J Neurochem 69, 1936-1944 (1997)) linearized with Bam HI. PCR templates for htt sense and antisense and sod1 antisense target RNAs were generated by amplifying 0.1 ng/ml (final concentration) plasmid template encoding htt or sod1 cDNA using the following primer pairs: htt sense target, 5'-GCG TAA TAC GAC TCA CTA TAG GAA CAG TAT GTC TCA GAC ATC-3' (SEQ ID NO:1) and 5'-UUCG AAG UAU UCC GCG UAC GU-3' (SEQ ID NO:2); htt antisense target, 5'-GCG TAA TAC GAC TCA CTA TAG GAC AAG CCT AAT TAG TGA TGC-3' (SEQ ID NO:3) and 5'-GAA CAG TAT GTC TCA GAC ATC-3' (SEQ ID NO:4); sod1 antisense target, 5'-GCG TAA TAC GAC TCA CTA TAG GGC TTT GTT AGC AGC CGG AT-3' (SEQ ID NO:5) and 5'-GGG AGA CCA CAA CGG TTT CCC-3' (SEQ ID NO:6).

RISC Extract Preparation

*Drosophila* embryo lysate preparation, in vitro RNAi reactions, and cap-labeling of target RNAs using guanylyl transferase were carried out as previously described (Tuschl et al., 1999, supra; Zamore et al., 2000, supra). Target RNAs were used at ~5 nM concentration to ensure that reactions occurred under single-turnover conditions. Target cleavage under these conditions was proportionate to siRNA concentrations. Cleavage products of RNAi reactions were analyzed by electrophoresis on 5% or 8% denaturing acrylamide gels. 5' end labeling and determination of siRNA unwinding status were according to Nykänen et al. (Nykänen et al., 2001, supra) except that unlabeled competitor RNA was used at 100-fold molar excess. Gels were dried, then exposed to image plates (Fuji), which were scanned with a Fuji FLA-5000 phosphorimager. Images were analyzed using Image Reader FLA-5000 version 1.0 (Fuji) and Image Gauge version 3.45 or 4.1 (Fuji). Data analysis was performed using Excel (Microsoft) and Igor Pro 5.0 (Wavemetrics).

Example 1

Functionally Asymmetric siRNA Duplexes Having a Single Blunt End

The following example describes methods for constructing single blunt-ended siRNA duplexes capable of selectively entering a RISC-mediated RNAi pathway and selectively cleaving a test target for destruction.

Figure 4:
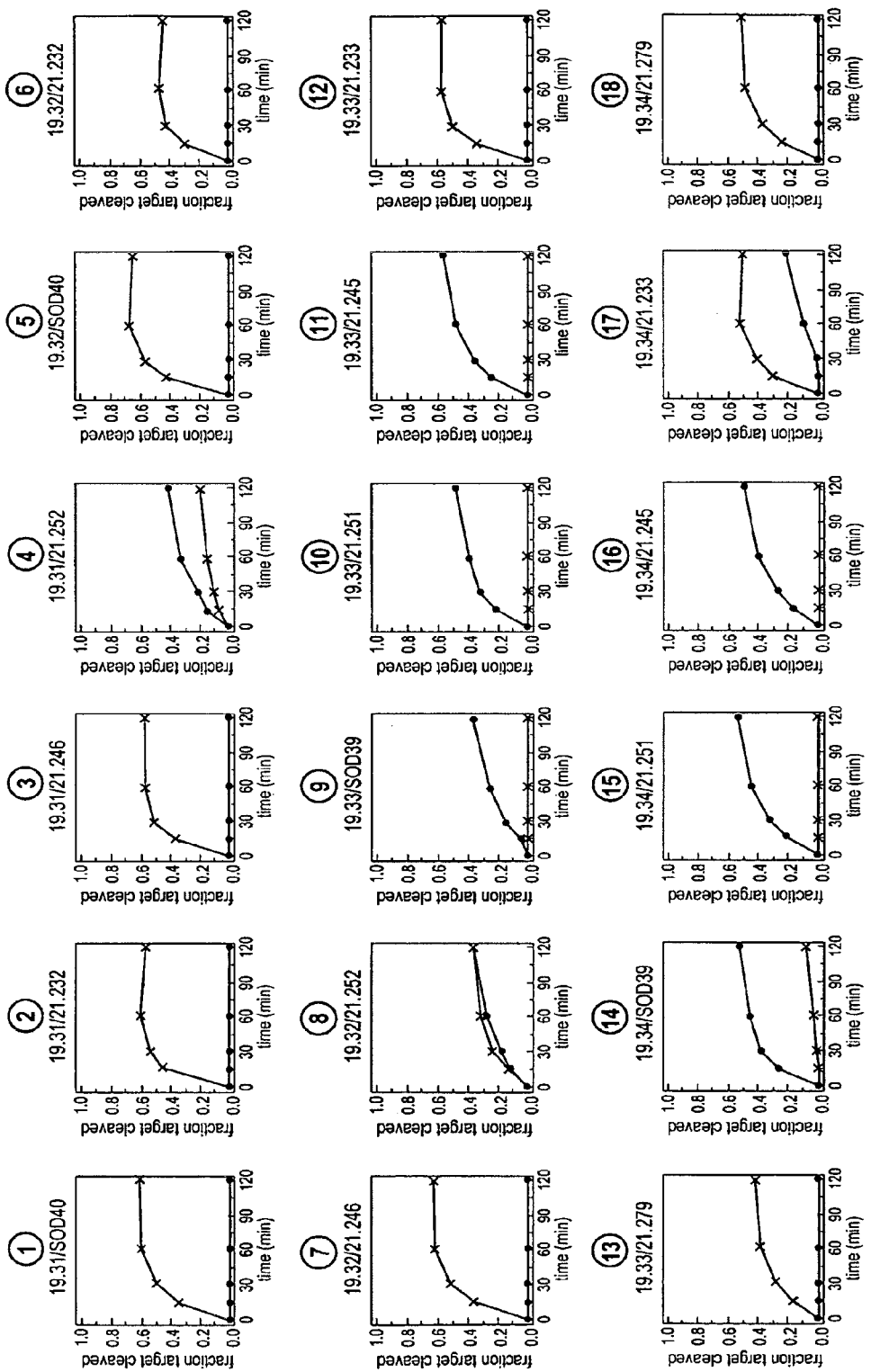
FIG. 4 shows the efficacy and specificity of the single blunt-ended siRNA duplexes and their ability to cleave sense and antisense gene targets using *Drosophila* extracts that provide a functional RISC-mediated RNAi pathway. Black (x) data points show % antisense gene target cleaved (SOD1 sense target; i.e., gene knockdown) whereas red (O) data points show % sense gene target cleaved.

Briefly, to assess quantitatively if the two strands of an siRNA duplex having a single 5' or 3' blunt end are equally competent to direct RNAi, the individual rates of sense and antisense target cleavage for a single blunt-ended siRNA duplex directed against the SOD1 target gene were examined (FIG. 4). The relevant portions of the sense and antisense target RNA sequences are shown in FIG. 4 and in schematic form in FIG. 1 (see lower panel). The single blunt-ended siRNA duplex effectively silences SOD1 expression in *Drosophila* extracts when having a weakened 5' end (i.e., "frayed end") (compare 4 with 1 in FIGS. 1 and 4). Accordingly, these results indicate that 1) a single blunt end siRNA is functional and 2) that weakening the 5' antisense base pair interaction with the 3' sense strand dramatically increases entry of the antisense strand into the complex and subsequent gene knockdown activity.

Example 2

Functionally Asymmetric siRNA Duplexes Having a Double Blunt Ends

The following example describes methods for constructing double blunt-ended siRNA duplexes capable of selectively entering a RISC-mediated RNAi pathway and selectively cleaving a test target for destruction.

Figure 5:
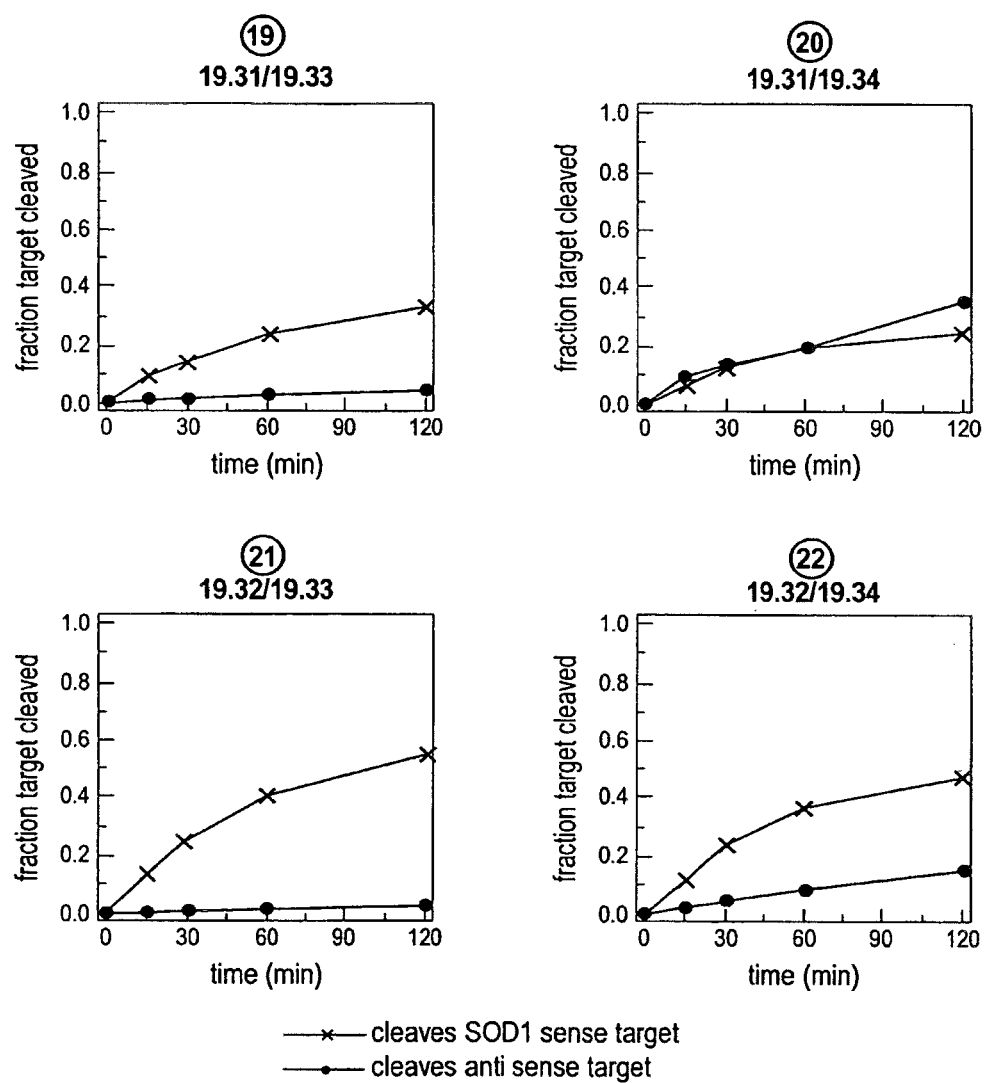
FIG. 5 shows the efficacy and specificity of the double blunt-ended siRNA duplexes and their ability to cleave sense and antisense gene targets using *Drosophila* extracts that provide a functional RISC-mediated RNAi pathway. Black (x) data points show % antisense gene target cleaved (SOD1 sense target; i.e., gene knockdown) whereas red (O) data points show % sense gene target cleaved.

Briefly, to assess quantitatively if the two strands of an double blunt-ended siRNA duplex are equally competent to direct RNAi, the individual rates of sense and antisense target cleavage for a single blunt-ended siRNA duplex directed against the SOD1 target gene were examined (FIG. 5). The relevant portions of the sense and antisense target RNA sequences are shown in FIG. 3 and in schematic form in FIG. 2 (see lower panel). The double blunt-ended siRNA duplexes effectively silence SOD1 expression in *Drosophila* extracts and this activity is increased in the when having a weakened 5' end (i.e., "frayed end") (compare 4 with 1 in FIGS. 1 and 4).

Figure 2:
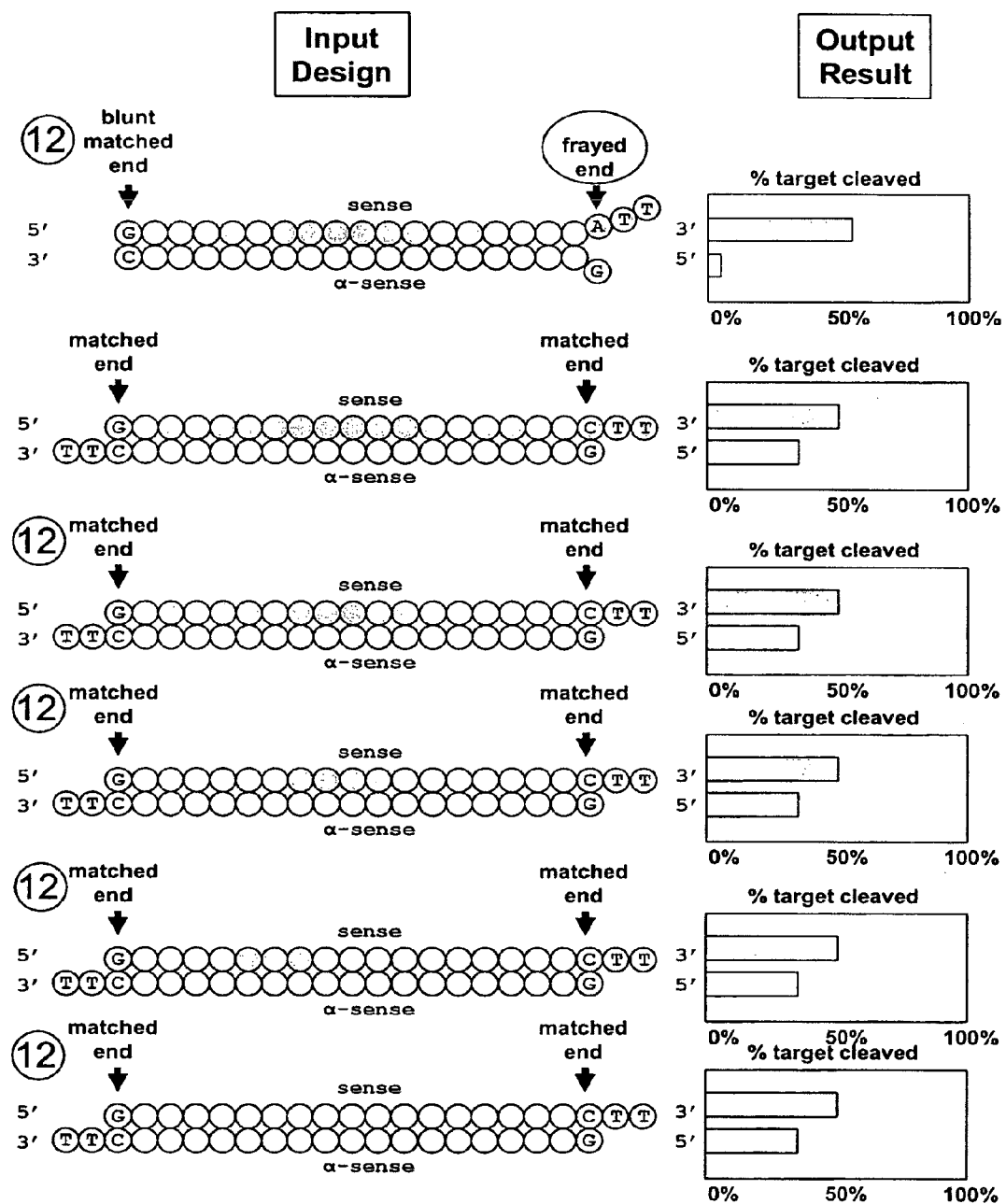
FIG. 2 shows a schematic of the structural and functional characteristics of siRNAs of the invention having both 5' and 3' blunt ends. Selected double blunt-ended siRNAs with either a 5' or 3' frayed end are shown as well as their corresponding ability to target cleavage of a sense and/or antisense gene target. Numbers on the left correspond to the siRNA shown in further detail structurally in FIG. 4 and tested for target specificity in FIG. 5.

Accordingly, these results indicate that 1) double blunt-end siRNA molecules are functional and 2) that weakening the 5' antisense base pair interaction with the 3' sense strand or the 5' sense base pair interaction with the 3' antisense strand modulates the entry of the antisense and sense strand into the complex and subsequent gene knockdown activity (see FIGS. 2 and 5).

Example 3

Single and Double Blunt-Ended siRNA Strand Contribution in RISC Assembly

The following example describes methods for determining RISC-mediated selectivity regarding the single and double blunt-ended siRNAs of the invention.

To identify the source of asymmetry in the function of such an single or double blunt-ended siRNA duplex, the unwinding of the two siRNA strands when the duplex is incubated in a standard in vitro RNAi reaction is measured. This assay has been observed to determine accurately the fraction of siRNA that is unwound in an ATP-dependent step in the RNAi pathway and that no functional RISC is assembled in the absence of ATP (Nykänen et al., 2001). Other observations have noted that siRNA unwinding correlates with capacity of an siRNA to function in target cleavage (Nykänen et al., 2001, supra; Martinez et al., Cell 110, 563-574 (2002)), demonstrating that siRNA duplex unwinding is required to assemble a RISC competent to base pair with its target RNA.

Accordingly, the accumulation of single stranded siRNA against a test gene such as luciferase after 1 hour incubation in an in vitro RNAi reaction in the absence of target RNA is measured. After one hour of incubation with Drosophila embryo lysate in a standard RNAi reaction, the antisense strand of the luciferase siRNA is converted to single-strand. In control experiments, single-stranded RNA is assayed without incubation in lysate. Since the production of single-stranded antisense siRNA must be accompanied by an equal amount of single-stranded sense siRNA, the missing sense-strand is calculated to have been destroyed after unwinding.

To establish that the observed asymmetry in the accumulation of the two single-strands is not an artifact of our unwinding assay, an independent method for measuring the fraction of siRNA present as single-strands in protein-RNA complexes is performed. In this assay, double-stranded siRNA is incubated with Drosophila embryo lysate in a standard RNAi reaction for 1 h, then a 31 nt 2'-O-methyl RNA oligonucleotide containing a 21 nt sequence complementary to the radiolabeled siRNA strand is added. 2'-O-methyl oligonucleotides are not cleaved by the RNAi machinery, but can bind stably to complementary siRNA within the RISC. To allow recovery of RISC, the 2'-O-methyl oligonucleotide is tethered to a magnetic bead via a biotin-streptavidin linkage. After washing away unbound RNA and protein, the amount of radioactive siRNA bound to the bead is measured. The assay is performed with separate siRNA duplexes in which either the sense or the antisense strand is 5'-$^{32}$P-radiolabeled. Capture of $^{32}$P-siRNA is observed when the 2'-O-methyl oligonucleotide contained a 21-nt region complementary to the radiolabeled siRNA strand, but not when an unrelated oligonucleotide is used.

Thus, the above assay captures all RISC activity directed by the siRNA strand complementary to the tethered oligonucleotide, demonstrating that it measures siRNA present in the lysate as single-strand complexed with RISC proteins.

Accordingly, this assay can determine the contribution each strand from a single or double blunt-ended siRNA of the invention makes to RISC assembly.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of enhancing silencing of a target mRNA comprising providing a double stranded RNA (dsRNA) comprising a sense strand and an antisense strand, wherein the base pair strength between the antisense strand 5' end (AS 5') and the sense strand 3' end (S 3') is less than the base pair strength between the antisense strand 3' end (AS 3') and the sense strand 5' end (S 5'), wherein said dsRNA comprises a frayed AS 5' comprising a base pair mismatch, such that the antisense strand preferentially guides cleavage of a target mRNA, and wherein said AS 3' is lacking an overhang and wherein said S 3' comprises an overhang.

2. The method of claim 1, wherein said target mRNA comprises the nucleotide sequence of SEQ ID NO: 9 (SOD1).

3. The method of claim 2, wherein said sense strand comprises the nucleotide sequence of 5' GAGACUUGGG CAAUGUGAA 3' (SEQ ID NO:13).

4. The method of claim 2, wherein said antisense strand comprises the nucleotide sequence of 5' GUCACAUUGC CCAAGUCUC 3' (SEQ ID NO:15).

5. The method of claim 2, wherein said sense strand comprises the nucleotide sequence of 5' GAGACUUGGG CAAUGUGAA 3' (SEQ ID NO:13) and said antisense strand comprises the nucleotide sequence of 5' GUCACAUUGC CCAAGUCUC 3' (SEQ ID NO:15).

6. The method of claim 1, wherein each strand of the dsRNA has a length of between about 19 nucleotides and about 22 nucleotides.

7. The method of claim 1, wherein the S 3' comprises a two nucleotide overhang.

8. The method of claim 1, wherein the S 3' comprises a dTdT overhang.

9. The method of claim 1, wherein said dsRNA is provided as an shRNA which is processed by a cell to yield the dsRNA.

10. The method of claim 9, wherein a viral construct encodes the shRNA.

* * * * *

SEQUENCE LISTING

<160> NUMBER OF SEQ ID NOS: 21

<210> SEQ ID NO 1
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gcgtaatacg actcactata ggaacagtat gtctcagaca tc                          42

<210> SEQ ID NO 2
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
uucgaaguau uccgcguacg u                                                 21

<210> SEQ ID NO 3
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 3
gcgtaatacg actcactata ggacaagcct aattagtgat gc                          42

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
gaacagtatg tctcagacat c                                                 21

<210> SEQ ID NO 5
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gcgtaatacg actcactata gggctttgtt agcagccgga t                           41

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
gggagaccac aacggtttcc c                                                 21

<210> SEQ ID NO 7
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gagacuuggg caaugugac                                                    19

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
gucacauugc ccaagucuct t                                                 21
```

```
<210> SEQ ID NO 9
<211> LENGTH: 54
<212> TYPE: RNA
<213> ORGANISM: Drosophila sp.

<400> SEQUENCE: 9
gaugaagaga ggcauguugg agacuugggc aaugugacug cugacaaaga uggu          54

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
uucacauugc ccaagucuct t                                              21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: Inosine

<400> SEQUENCE: 11
nucacauugc ccaagucuct t                                              21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
gucacauugc ccaagucuat t                                              21

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
```
gagacuuggg caaugugaa                                              19

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
gagacuuggg caaugugact t                                           21

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gucacauugc ccaagcuc                                               19

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
uagacuuggg caaugugact t                                           21

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: Inosine

<400> SEQUENCE: 17
nagacuuggg caaugugact t                                           21

<210> SEQ ID NO 18
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
gagacuuggg caaugugaat t                                               21

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
gagacuuggg caaugugaut t                                               21

<210> SEQ ID NO 20
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
gucacauugc ccaagucua                                                  19

<210> SEQ ID NO 21
<211> LENGTH: 54
<212> TYPE: RNA
<213> ORGANISM: Drosophila sp.

<400> SEQUENCE: 21
accaucuuug ucagcaguca cauugcccaa gucuccaaca ugccucucuu cauc           54
```